(12) United States Patent
Marchal et al.

(10) Patent No.: US 7,820,142 B2
(45) Date of Patent: Oct. 26, 2010

(54) IMMUNOGENIC GLYCOPEPTIDES, SCREENING, PREPARATION AND USES

(75) Inventors: Gilles Marchal, Ivry-sur-Seine (FR);
Félix Romain, Fontenay-les-Briis (FR);
Pascale Pescher, Issy les Moulineaux (FR); Françoise Baleux, Paris (FR);
Daniel Scott-Algara, Champigny-sur-Marne (FR); Laurence Mulard, Le Kremlin-Bicêtre (FR)

(73) Assignee: Institut Pasteur, Paris (FR)

( * ) Notice: Subject to any disclaimer, the term of this patent is extended or adjusted under 35 U.S.C. 154(b) by 1061 days.

(21) Appl. No.: 10/953,095

(22) Filed: Sep. 30, 2004

(65) Prior Publication Data

US 2006/0067888 A1 Mar. 30, 2006

(51) Int. Cl.
*A61K 49/00* (2006.01)
(52) U.S. Cl. .................. 424/9.1; 424/9.2; 424/184.1; 424/234.1; 424/248.1
(58) Field of Classification Search ............... 424/1.11, 424/1.65, 1.69, 9.1, 9.2, 168.1, 234.1, 248.1, 424/278, 282.1, 184.1, 185.1, 186.1, 190.1, 424/193.1; 434/4, 41, 71.1, 325, 363, 366, 434/372, 820
See application file for complete search history.

(56) References Cited

U.S. PATENT DOCUMENTS 7,361,348 B2 * 4/2008 Marchal et al. .......... 424/184.1

FOREIGN PATENT DOCUMENTS

| WO | 96/23885 | 8/1996 |
|---|---|---|
| WO | 98/16646 | 4/1998 |
| WO | 98/29132 | 7/1998 |

OTHER PUBLICATIONS

U.S. Appl. No. 12/034,926, filed Feb. 21, 2008, Marchal, et al.
U.S. Appl. No. 11/576,203, filed Mar. 28, 2007, Marchal et al.
Karen M. Dobos, et al., "Definition of the Full Extent of Glycosylation of the 45-Kilodalton Glycoprotein of *Mycobacterium tuberculosis*" Journal of Bacteriology, May 1996, pp. 2498-2506.
Henrikl Franzyk, et al., "Synthesis of aliphatic *O*-dimannosyl amino acid building blocks for solid-phase assembly of glycopeptide libraries", J. Chem. Soc. Perkin Trans.1, (1995), pp. 2883-2898.
Felix Romain, et al., "Deglycosylation of the 45/47-Kilodalton Antigen Complex of *Mycobacterium tuberculosis* Decreases Its Capacity to Elicit in Vivo or in Vitro Cellular Immune Responses", Infection and Immunity, Nov. 1999, pp. 5567-5572, vol. 67, No. 11.

* cited by examiner

*Primary Examiner*—D L Jones
(74) *Attorney, Agent, or Firm*—Oblon, Spivak, McClelland, Maier & Neustadt, L.L.P.

(57) ABSTRACT

The invention relates to immunogenic glycopeptides derived from pathogenic microorganisms, which can be used for immunization and diagnosing infections dye to such pathogenic microorganisms and also to method for the selection and preparation thereof.

8 Claims, 10 Drawing Sheets

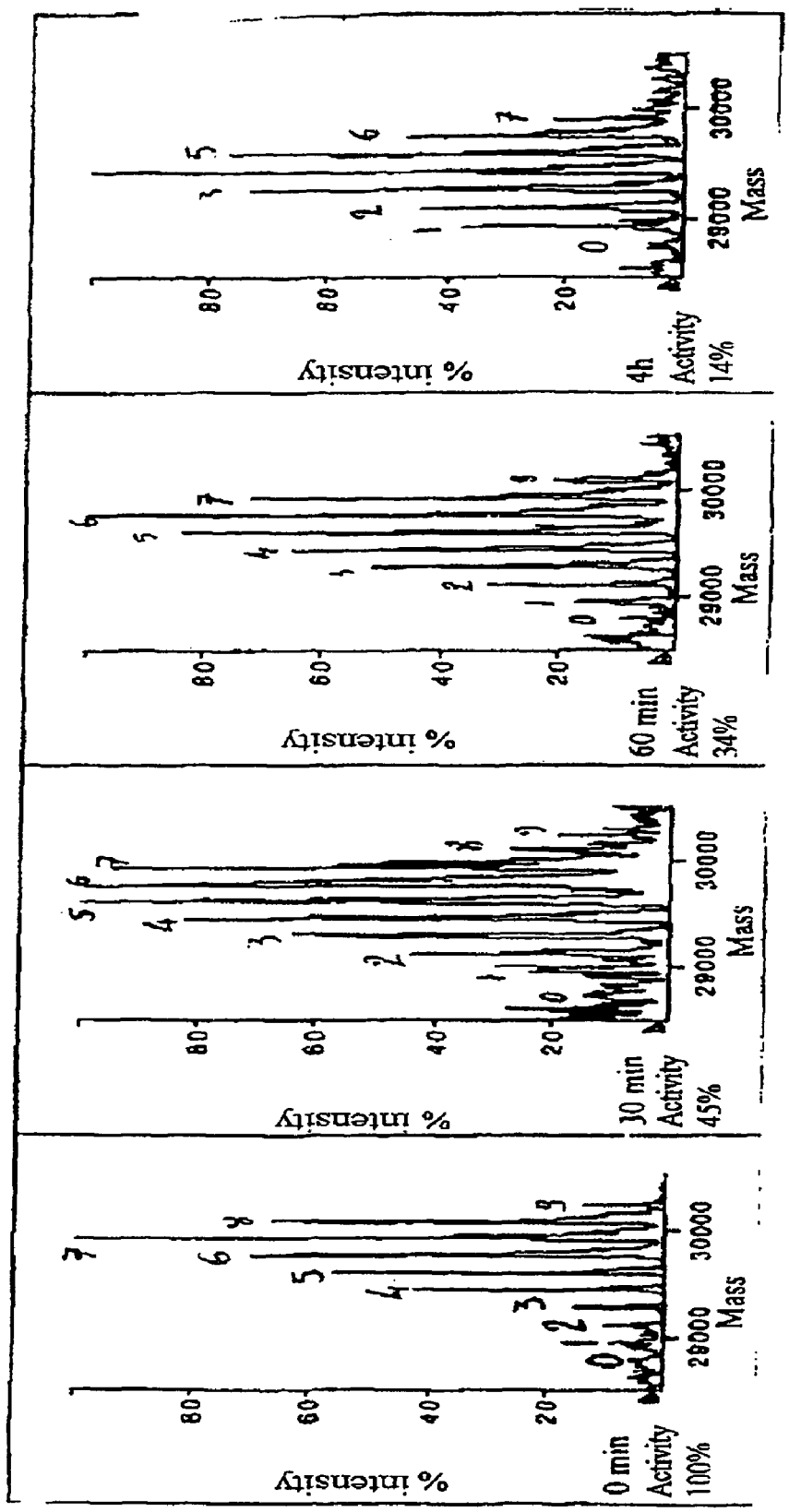
FIGURE 2.1

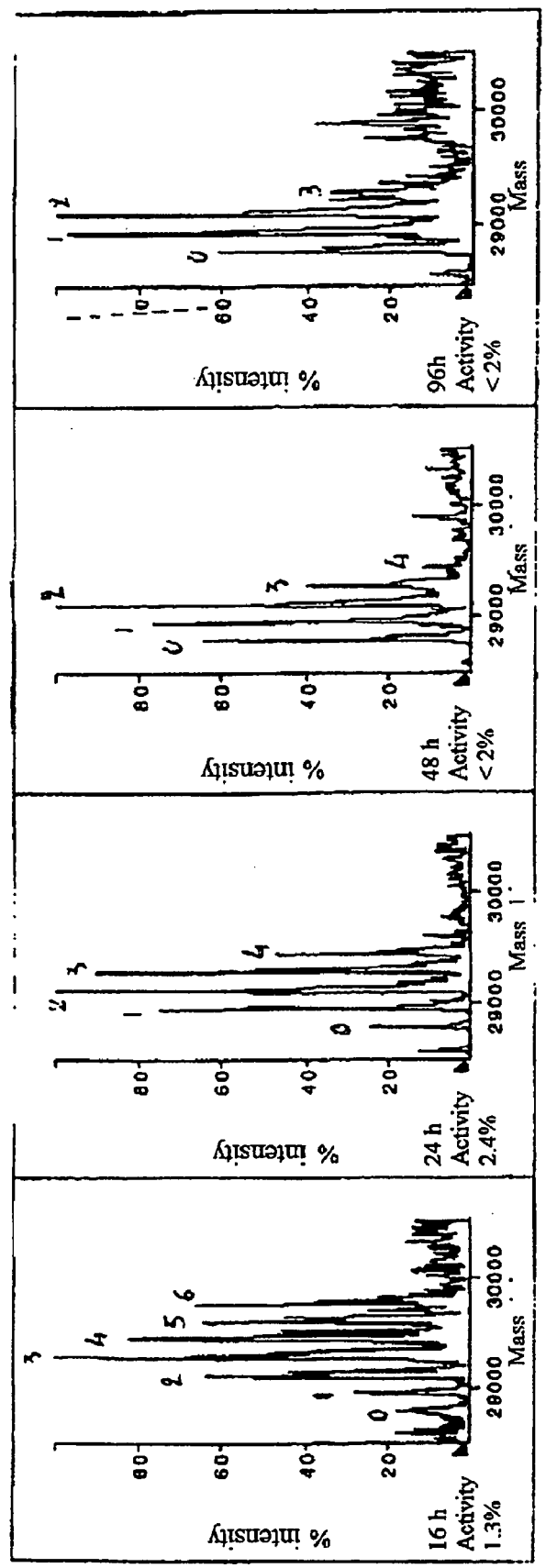
FIGURE 2.2

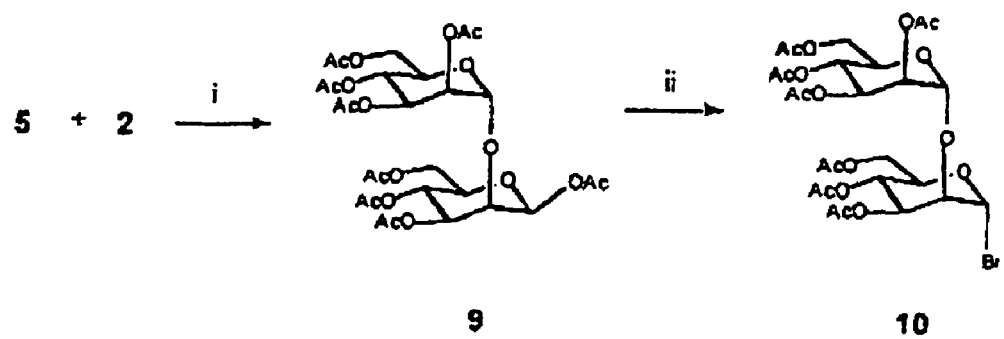
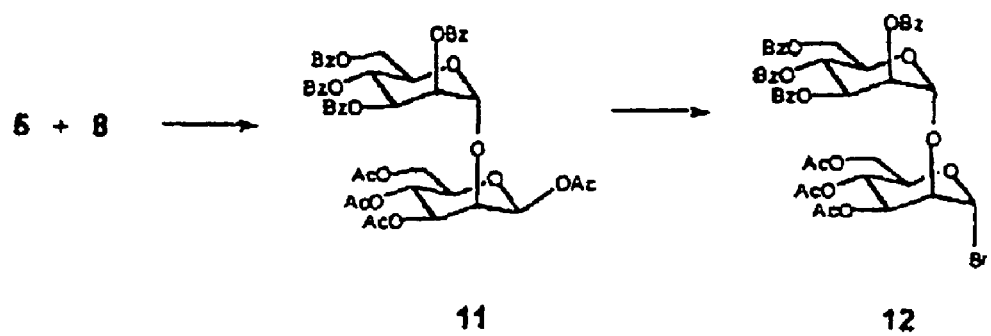
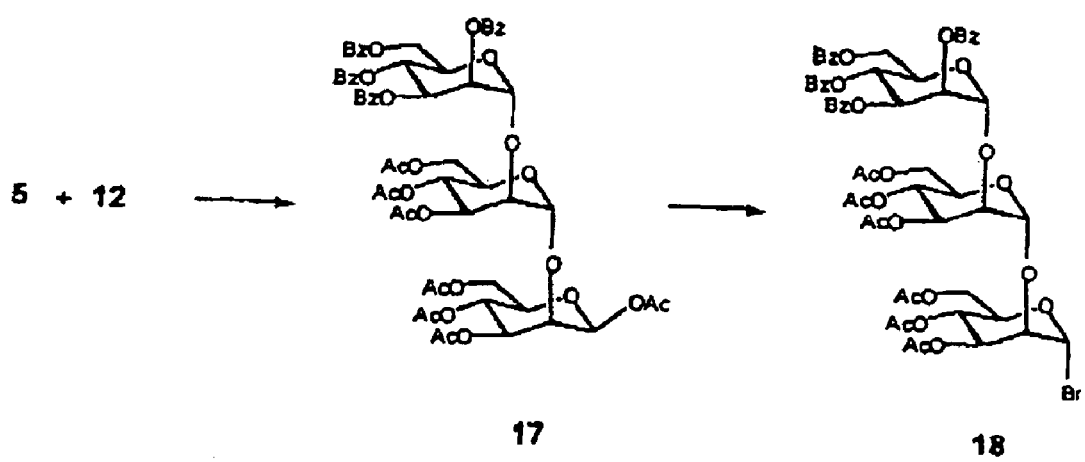
FIGURE 7a

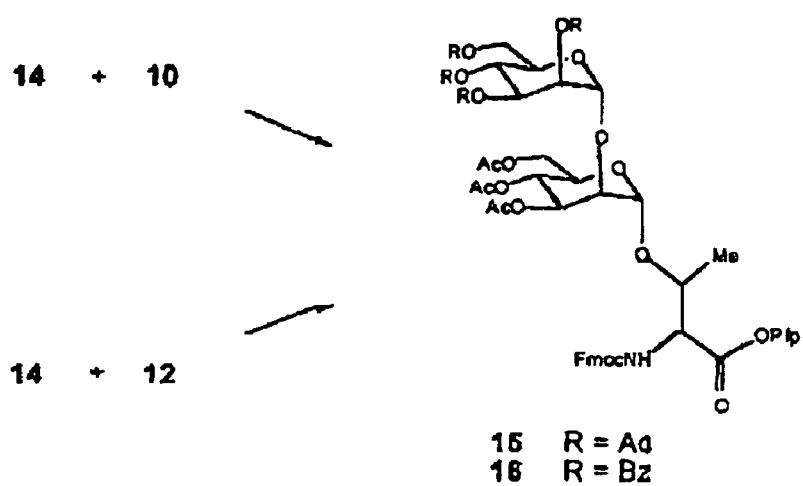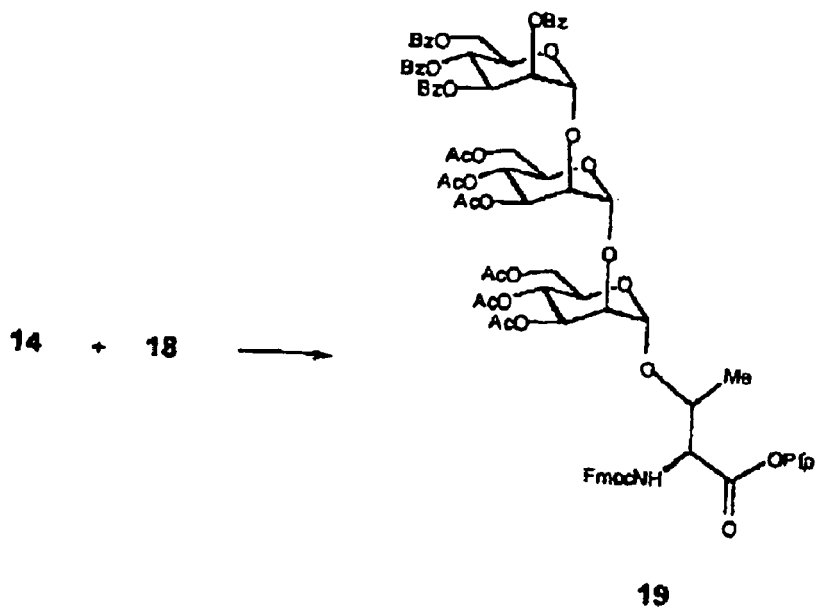
FIGURE 7b

SEQUENCE LISTING

<160> NUMBER OF SEQ ID NOS: 11

<210> SEQ ID NO 1
<211> LENGTH: 39
<212> TYPE: PRT
<213> ORGANISM: Mycobacterium tuberculosis
<220> FEATURE:
<221> NAME/KEY: MOD_RES
<222> LOCATION: (10)..(10)
<223> OTHER INFORMATION: glycosidic bond to a di- or tri-saccharide
<220> FEATURE:
<221> NAME/KEY: MOD_RES
<222> LOCATION: (18)..(18)
<223> OTHER INFORMATION: glycosidic bond to a di- or tri-saccharide
<220> FEATURE:
<221> NAME/KEY: MOD_RES
<222> LOCATION: (27)..(27)
<223> OTHER INFORMATION: glycosidic bond to a di- or tri-saccharide

<400> SEQUENCE: 1

Asp Pro Glu Pro Ala Pro Pro Val Pro Thr Thr Ala Ala Ser Pro Pro
1               5                   10                  15

Ser Thr Ala Ala Ala Pro Pro Ala Pro Ala Thr Pro Val Ala Pro Pro
            20                  25                  30

Pro Pro Ala Ala Ala Asn Thr
        35

<210> SEQ ID NO 2
<211> LENGTH: 26
<212> TYPE: PRT
<213> ORGANISM: Mycobacterium tuberculosis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (17)..(17)
<223> OTHER INFORMATION: glycosidic bond to a di- or tri-saccharide

<400> SEQUENCE: 2

Pro Ala Pro Ala Pro Ala Pro Ala Gly Glu Val Ala Pro Thr Pro Thr
1               5                   10                  15

Thr Pro Thr Pro Gln Arg Thr Leu Pro Ala
            20                  25

<210> SEQ ID NO 3
<211> LENGTH: 35
<212> TYPE: PRT
<213> ORGANISM: Mycobacterium tuberculosis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: glycosidic bond to a di- or tri-saccharide
<220> FEATURE:
<221> NAME/KEY: MOD_RES
<222> LOCATION: (5)..(5)
<223> OTHER INFORMATION: glycosidic bond to a di- or tri-saccharide
<220> FEATURE:
<221> NAME/KEY: MOD_RES
<222> LOCATION: (7)..(7)
<223> OTHER INFORMATION: glycosidic bond to a di- or tri-saccharide
<220> FEATURE:
<221> NAME/KEY: MOD_RES
<222> LOCATION: (13)..(13)

```
<223> OTHER INFORMATION: glycosidic bond to a di- or tri-saccharide
<220> FEATURE:
<221> NAME/KEY: MOD_RES
<222> LOCATION: (15)..(15)
<223> OTHER INFORMATION: glycosidic bond to a di- or tri-saccharide
<220> FEATURE:
<221> NAME/KEY: MOD_RES
<222> LOCATION: (23)..(23)
<223> OTHER INFORMATION: glycosidic bond to a di- or tri-saccharide
<220> FEATURE:
<221> NAME/KEY: MOD_RES
<222> LOCATION: (25)..(25)
<223> OTHER INFORMATION: glycosidic bond to a di- or tri-saccharide

<400> SEQUENCE: 3

Thr Ile Pro Thr Thr Glu Thr Pro Pro Pro Pro Gln Thr Val Thr Leu
 1               5                  10                  15

Ser Pro Val Pro Pro Gln Thr Val Thr Val Ile Pro Ala Pro Pro Pro
            20                  25                  30

Glu Glu Gly
        35

<210> SEQ ID NO 4
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 4
caacgttggg cc                                                          12

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
tcccaagctt ttggtagccg                                                  20

<210> SEQ ID NO 6
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 6
ctaggatcca ccatgccgga gccagcgccc cc                                    32

<210> SEQ ID NO 7
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 7
gatccggggg ggaacgttgg ggggg                                            25

<210> SEQ ID NO 8
<211> LENGTH: 25
<212> TYPE: DNA
<213> ORGANISM: Artificial Sequence
<220> FEATURE:
```

-continued

```
<223> OTHER INFORMATION: synthetic oligonucleotide

<400> SEQUENCE: 8
gatccccccc caacgttccc ccccg                                          25

<210> SEQ ID NO 9
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 9
agcgctatga cgttccaagg gccc                                           24

<210> SEQ ID NO 10
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 10
gggcccttgg aacgtcatag cgct                                           24

<210> SEQ ID NO 11
<211> LENGTH: 35
<212> TYPE: PRT
<213> ORGANISM: Mycobacterium tuberculosis
<220> FEATURE:
<221> NAME/KEY: MOD_RES
<222> LOCATION: (29)..(29)
<223> OTHER INFORMATION: glycosidic bond to a mannose, a di-mannose or
      a tri-mannose

<400> SEQUENCE: 11

Val Ala Pro Pro Pro Ala Pro Ala Pro Ala Pro Ala Glu Pro Ala Pro
1               5                   10                  15

Ala Pro Ala Pro Ala Gly Glu Val Ala Pro Thr Pro Thr Thr Pro Thr
            20                  25                  30

Pro Gln Arg
        35
```

IMMUNOGENIC GLYCOPEPTIDES, SCREENING, PREPARATION AND USES

The present invention relates to immunogenic glycopeptides derived from pathogenic microorganisms, which can be used for immunization and diagnosing infections due to such pathogenic microorganisms (bacteria or fungi), and also to the methods for the selection and for the preparation thereof.

The means implemented for preventing and treating these infections comprise, firstly, screening which enables the infection to be monitored and treated and, secondly, immunization.

These means are illustrated hereinafter, taking as an example one of the most serious infections in human medicine: infection with *M. tuberculosis*. Specifically, 5 to 10% of individuals infected with *M. tuberculosis* who have a normal immune response develop a serious disease (tuberculosis); this frequency is even higher in individuals who have a deficiency in their immune response (infection with HIV, treatment with immunosuppressors, etc.).

Diagnosis

Among the various techniques currently available, mention may be made of:
- the production of pure cultures of *M. tuberculosis*, which is the most rigorous means for diagnosing tuberculosis with certitude. It is a moderately sensitive technique which enables diagnosis for ⅔ of the cases of pulmonary tuberculosis. The results are available only after a minimum delay of 3-4 weeks, sometimes only after culturing for 2 months. The use of culturing techniques employing labelled precursors makes it possible to shorten these delays, which nevertheless remain considerable. This detection of *M. tuberculosis* by culturing requires a sample containing bacilli, which is sometimes difficult to obtain even for pulmonary tuberculosis, in which approximately ⅓ of cases do not receive biological confirmation. Sometimes, this examination requires a specialized medical intervention (lumbar puncture of the cerebrospinal fluid or lymph node biopsy) for extrapulmonary forms of the disease.
- microbiological techniques based on molecular genetics (PCR) are confronted with the same requirement of obtaining a sample containing bacteria. Moreover, because of the presence, in the sample, of PCR reaction inhibitors, the origin of which is impossible to control, these techniques are sometimes unusable. They have not been validated in common practice.
- at the current time, there is no serodiagnosis which has a sensitivity and a specificity compatible with diagnostic use.
- the reaction to tuberculin shows that an individual is sensitized, has been infected with *M. tuberculosis* or has been immunized with BCG. Tuberculin is, in fact, a mixture of *M. tuberculosis* antigens and is therefore incapable of making a distinction between an infection with *M. tuberculosis* and immunization with BCG, because of the very many cross-reactions between the antigens of the vaccine and *M. tuberculosis*. In addition, this reaction to tuberculin does not make it possible to distinguish a tuberculosis, which is an active disease, from an infection with *M. tuberculosis*.

Vaccine

Immunization with BCG makes it possible to control the primary infection (initial multiplication of *M. tuberculosis*) but especially the secondary dissemination of these bacilli. It probably contributes to decreasing the incidence of latent infections against which no effective treatment is currently available. BCG has been used to immunize more than 3 billion individuals against tuberculosis, without any particular side effects. During immunization with BCG, there is a local multiplication of these bacilli, of attenuated virulence. Cellular immunity is induced. It causes delayed-type hypersensitivity (HSR) directed against the proteins or antigens of mycobacteria (reaction to tuberculin), and increased resistance to infection with *M. tuberculosis*. These two immune responses (HSR-type sensitization and increased resistance) are supported by T lymphocytes reacting with mycobacterial antigens.

BCG protects well against the acute forms of the infection (tubercular meningitis in children, for example). Its effectiveness is more variable in adults. The existence of a cross-reactivity between BCG and other mycobacteria which do not belong to the tuberculosis complex, and also the absence, in the BCG genome, of certain immunogenic antigens of *Mycobacterium tuberculosis*, or a different expression profile for these antigens during the infection, may explain the variable effectiveness of BCG.

In addition, BCG is a live strain of attenuated virulence. It therefore has a residual pathogenic power which prohibits the use thereof in immunodepressed individuals, in particular in individuals acknowledged to be infected with the human immunodeficiency virus (HIV).

In order to combat these infections more effectively, it would be judicious to have diagnostic tools and vaccines, in particular a "subunit" vaccine which therefore poses no danger, based on antigens which protect against the pathogenic microorganisms responsible for these infections.

A certain number of studies have been carried out in this sense, in order to find the molecule(s) of these pathogenic microorganisms, which is(are) capable of inducing a strong protective immune response. Thus, J. Hess et al. (C.R. Acad. Sci. Paris, 1999, 322: 953-958) have reviewed the properties which antigens able to be used as a vaccine against tuberculosis should have. In that review, they underline the importance of using a combination of preselected antigens rather than a single antigen. They recommend, in particular, selecting these antigens on the basis of criteria such as the presence of regions which are highly conserved among the various strains, the differences in the gene expression profile of the virulent strains and of the attenuated strains, the reactivity with respect to the effector cells of the immune response (B, CD4+ T, CD8+ T lymphocytes) or the capacity of these antigens to bind to the majority of HLA molecules of the major histocompatibility complex (MHC).

Some of these antigens are present either in the form of surface antigens, such as the mannoproteins of *C. albicans* (Buurman et al., *PNAS*, 1998, 95, 7670-7675), or in the form of secreted antigens, in *M. tuberculosis*: MPT59 (30 kDa), 85A (32 kDa), MPT64 (23 kDa), hsp71 (71 kfla), MPT51 (24 kDa), MPT63 (16 kDa) and ESAT-6 (6 kDa), (Andersen, *Infect. Immun.*, 1994, 62, 2536-2544; Horwitz et al., *PNAS*, 1995, 92, 1530-1534). These *M. tuberculosis* antigens have already been proposed as potential candidates for an immunization composition since they are preferentially recognized by CD4+ T lymphocytes (Andersen, et al., mentioned above; Horwitz et al., mentioned above).

It has also been proposed to isolate, from the *M. tuberculosis* antigens, peptides containing epitopes capable of being presented by an MHC class II molecule and of being recognized by specific CD4+ T lymphocytes; such epitopes have in particular been reported for two proteins: ESAT-6 (Olsen et al., *Eur. J. Immunol.*, 2000, 30, 1724-1732) and MPT-39 (Mustafa et al., *Inf. Immunol.*, 2000, 68, 3933-3940).

Several observations have previously been made by the inventors (Romain et al., *Inf. Immun.*, 1993, 61, 742-750; Romain et al. Proc. Natl. Acad. Sci. USA 1993, 90: 5322-5326):

only live bacteria are capable of inducing protective immunity, killed bacteria also inducing an immune response, but without protection;
 in the culture medium, proteins exist which are released by the bacteria, during their growth and which are capable of being recognized by the immune system of animals immunized with live bacteria, these being proteins which are poorly recognized or not at all after immunization with killed bacteria.

Using this double criterion of selection, two new proteins have been purified. A protein secreted by *M. tuberculosis*, named Apa, or MPT-32 or 45/47 kDa antigen complex, is the product of the Rv 1860 gene (Laqueyrerie et al. Infect. Immun. 1995, 63: 4003-4010). The second molecule is an internal peptide of a putative serine protease encoded by the Rv 1796 gene.

In using the native Apa protein as an antigen, the inventors have previously shown that this protein, which represents only 2% of the proteins secreted by the bacilli of the tuberculosis group (*M. tuberculosis, M. bovis* and BCG) in culture, is an immunodominant antigen which is very effectively recognized by specific CD4+ T lymphocytes originating from animals infected with *M. tuberculosis* or immunized with BCG (Romain et al., *Inf. Immun.*, 1999, 67, 5567-5572; Horn et al., *J. Biol. Chem.*, 1999, 274, 32023-32030).

In these same studies, the inventors also showed that mannosylation of Apa was essential for the antigenic activity of this protein:

demannosylation of Apa, obtained by treating native Apa with α-mannosidase or with trifluoromethanesulphonic acid (TFMS), or by expressing Apa in a bacterium incapable of glycosylating (*E. coli*) is accompanied by a 100-fold loss of antigenicity,
 glycosylated Apa produced by *Mycobacterium smegmatis*, which has an overall mannose composition which is slightly different from that of the Apa produced by *M. tuberculosis*, has an antigenic activity which is decreased approximately 10-fold.

Moreover, it has been reported that this *M. tuberculosis* Apa molecule contains 6 to 9 mannose residues linked, via a glycosidic bond of the α-(1,2) type, to 4 threonine residues ($T_{10}$, $T_{18}$, $T_{27}$ and $T_{277}$) in the following way: a dimannose ($T_{10}$ and $T_{18}$), a mannose ($T_{27}$), a mannose, a dimannose or a trimannose ($T_{277}$) (Dobos et al., *J. Bacteriol.*, 1996, 178, 2498-2506). It should be noted that this saccharide structure which contains mono-, di- or trimannoses resembles that of mannoproteins from yeast, in particular from *Candida albicans*, and is different from that of proteins from *F. meningosepticum*, which have longer oligomannose chains.

The loss of Apa antigenicity, observed after demannosylation, may be due to a decrease in the phagocytosis and processing of this antigen, or alternatively in the recognition of the latter by CD4+ T lymphocytes. Specifically, the mannose receptor of macrophages and of dendritic cells, which bind specifically to hexoses, in particular of mannoproteins from *C. albicans* and of mannolipids such as lipoarabinomannan from mycobacteria, plays a role in the phagocytosis and processing of antigens which are present at the surface of these cells in the form of a peptide/class II MHC molecule complex (Stahl et al., *Current Opinion in Immunology*, 1998, 10, 50-55). It has also been shown that a mannosylated peptide (mannosylated on lysine residues in the N-terminal position) is phagocytosed and processed by dendritic cells much more effectively than a non-glycosylated peptide with the same sequence (Tan et al., *Eur. J. Immunol.*, 1997, 27, 2426-2435).

In the chicken lysozyme model, it has been shown that peptides which are glycosylated analogues of a peptide constituting a T epitope of this antigen are capable of inducing CD4+ T lymphocytes which specifically recognize this glycosylated epitope (Deck et al., J. Immunol., 1995, 155, 1074-1078). However, since such glycosylated T epitopes specifically recognized by CD4+ T lymphocytes have not been identified in native antigens derived from pathogenic microorganisms (bacterium/fungus), the importance of glycosylation in the recognition of antigens from these pathogenic microorganisms by CD4+ T lymphocytes remains to be demonstrated.

In addition, and this being despite the data relating to *M. tuberculosis* Apa and general knowledge regarding the glycosylation of antigens, it has not, to date, been possible to prepare antigens derived from the O-glycosylated proteins of these pathogenic microorganisms, which can effectively be used in an immunogenic or immunization composition and/or in a diagnostic test.

Specifically:
 the active proteins which represent only a small percentage of the proteins produced by these microorganisms are purified with very low yields, using methods which are dangerous due to the handling of large amounts of these pathogenic agents,
 the proteins, produced in heterologous expression systems (eukaryotic cells or bacteria incapable of glycosylating), have a low antigenic activity,
 the proteins produced in homologous expression systems such as *M. smegmatis* have an acceptable antigenic activity but they are produced in insufficient amounts using complex methods.

Consequently, the inventors have set themselves the aim of preparing immunodominant antigens capable of inducing a protective humoral and/or cellular immune response, which, on the one hand, when administered alone or in combination with other antigens, may constitute a vaccine which can be used in all individuals, including immunodepressed individuals (disappearance of the risk linked to the use of a live vaccine) and, on the other hand, may be used for diagnostic purposes.

They have found that certain glycopeptides derived from pathogenic microorganisms which synthesize glycoproteins (and in particular mycobacteria) exhibit an antigenic activity which is at least equal, if not greater than, that of the deglycosylated native protein or of the recombinant protein produced in *E. coli*.

It is also an aim of the invention to develop means, which are simple to implement, for producing these glycopeptides in large amounts.

A subject of the present invention is immunogenic glycopeptides selected from the group consisting of:

$a_1$) glycopeptides essentially consisting of a glycosylated T epitope, comprising from 14 to 25 amino acids, among which at least one neutral amino acid is bonded to a disaccharide or to a trisaccharide (glycosidic bond) and at least 15% of said amino acids are prolines, one of the prolines being located in position -1 to -4, relative to the position of said neutral amino acid, which glycopeptides, derived from a pathogenic microorganism, are:

presented by a class II MHC molecule,
 specifically recognized by CD4+ T lymphocytes induced by immunization with the native glycoprotein from which they are derived, but are not recognized by the CD4+ T lymphocytes induced by immunization with a non-glycosylated peptide with the same sequence and capable of inducing a proliferation of said CD4+ T lymphocytes which recognize them and the secretion of cytokines by said lymphocytes, and b₁) glycopeptides which have a sequence of 15 to 39 amino acids including the sequence of the glycopeptide as defined in a₁), excluding the glycopeptide of sequence SEQ ID NO:11, derived from the Apa which is described by Dobos et al. (*J. Bacteriol.*, 1996, 178, 2498-2506).

These glycopeptides consisting essentially of a glycosylated T epitope are recognized by CD4+ T lymphocytes via this glycosylated T epitope. Specifically, after immunization with live bacilli of the tuberculosis group, there are many more T lymphocytes specific for these glycopeptides than T lymphocytes specific for the non-glycosylated peptides with the same sequence.

Advantageously, said glycopeptides have an antigenic activity which is at least 10 times greater, preferably at least 30 times greater, than that of a control peptide with the same sequence.

Said glycopeptides have the following advantages:
induction of a protective cellular-type immune response and possibly of a humoral response, and possible use as antigens in immunodepressed individuals,
antigenic activity at least equal to, if not greater than, conventional antigens (culture of said attenuated live microorganisms, mixtures of antigens prepared from said cultures or non-glycosylated peptides) since they are recognized by a greater number of T lymphocytes specific for the pathogenic microorganism,
very narrow specificity, which makes it possible both to eliminate the problems of cross-reactivity with other microorganisms, in particular with other atypical mycobacteria, and to increase the effectiveness of the immunization and of the diagnosis of the pathogenic microorganisms; specifically, they are more specific given that their oligosaccharide residues, which are present exclusively in said pathogenic microorganisms, contribute in an essential manner to the definition of the T epitope recognized by the CD4+ T lymphocytes; they thus constitute specific antigens for immunization and for diagnosing infections with pathogenic organisms capable of O-glycosylating some of their proteins (bacilli of the tuberculosis complex, *Flavobacterium meningosepticum*, *Candida albicans*, etc.),
use in immunodepressed individuals since they are totally apathogenic,
production possible in large amounts,
better standardization of active doses and of the effectiveness of the vaccine,
ease of storage and of use.

According to an advantageous embodiment of said glycopeptides, said neutral amino acids are selected from the group consisting of serine and threonine.

According to an advantageous arrangement of this embodiment of said glycopeptides, they contain from 1 to 7 threonine residues bonded to a disaccharide or to a trisaccharide.

According to another advantageous embodiment of said glycopeptides, said disaccharide or trisaccharide is a dimer or a trimer of hexose, preferably a mannose.

According to yet another advantageous embodiment of said glycopeptides, said glycosidic bond is an α-(1,2) bond.

According to yet another advantageous embodiment, said glycopeptides are derived from a pathogenic microorganism capable of O-glycosylating proteins, preferably *Mycobacterium tuberculosis* or *Candida albicans*.

In accordance with the invention, said glycopeptides are preferably derived:
from the Apa protein of *M. tuberculosis* (Genbank number X80268) or
from the Rv1796 protein encoded by the Rv 1796 gene, with reference to the annotation of the sequence of the genome of *M. tuberculosis* strain H37Rv (Sanger bank).

Preferably, said glycopeptide is selected from the group consisting of:
a 39 amino acid glycopeptide, the sequence (SEQ ID NO:1) of which is that which extends from positions 1 to 39 of the sequence of the Apa protein and in which at least one of the threonine residues in position 10, 18 and 27 of SEQ ID NO:1 is bonded to a disaccharide or trisaccharide via a glycosidic bond,
a 26 amino acid glycopeptide, the sequence (SEQ ID NO:2) of which is that which extends from positions 261 to 286 of the sequence of the Apa protein (C-terminal sequence) and in which the threonine residue in position 17 of SEQ ID NO:2 is bonded to a disaccharide or trisaccharide via a glycosidic bond, and
a 35 amino acid glycopeptide, the sequence (SEQ ID NO:3) of which is that which extends from positions 169 to 203 of the sequence of the Rv 1796 protein and in which at least one of the threonine residues in position 4, 5, 7, 13, 15, 23 and 25 of SEQ ID NO:3 is bonded to a disaccharide or trisaccharide via a glycosidic bond.

A subject of the invention is also a method for synthesizing a glycopeptide as defined above, characterized in that it comprises the following steps:
preparing, in solution, glycosylated neutral amino acids bonded to a disaccharide or to a trisaccharide via a glycosidic bond,
synthesizing the glycopeptide, on a solid support, using the amino acids required for producing the peptide sequence of said glycopeptide and the glycosylated neutral amino acids obtained above, and
cleaving the glycopeptide from the solid support.

According to an advantageous embodiment of said method, said neutral amino acid is selected from the group consisting of serine and threonine.

According to an advantageous arrangement of this embodiment, when said glycopeptides have the following sequences (T represents an O-glycosylated threonine functionalized with 2 or 3 glycosidic residues, and Ac represents an acetate function):

```
SEQ ID NO: 1:
H₂N-DPEPAPPVPTTAASPPSTAAAPPAPATPVAPPPPAPAAAT-CONH₂

SEQ ID NO: 2:
AcNH-PAPAPAPAGEVAPTPTTPTPQRTLPA-COOH

SEQ ID NO: 3:
AcNH-TIPTTETPPPPQTVTLSPVPPQTVTVIPAPPPEEG-CONH₂,
``` said method comprises the following steps:
i) preparing, in solution, O-glycosylated threonines functionalized with 2 or 3 glycosidic residues,
ii) synthesizing the peptides corresponding to the sequences SEQ ID NO:1, SEQ ID NO:2 and SEQ ID NO:3 mentioned above, on a solid support, using the amino acids required for producing these sequences and the O-glycosylated threonines obtained in step i), iii) cleaving the peptides from the solid support, and iv) introducing, by chemical synthesis, an amide function at the C-terminal end of the peptides SEQ ID NO:1 and SEQ ID NO:3, and an acetate function at the N-terminal end of the peptides SEQ ID NO:2 and SEQ ID NO:3.

The synthesis of the peptides SEQ ID NO:1, SEQ ID NO:2 and SEQ ID NO:3 therefore corresponds to a conventional solid-phase peptide synthesis during which glycosylated amino acids are introduced. As is known in the field of solid-phase peptide synthesis, the amino acids used are suitably protected and, if necessary, activated before being incorporated one after the other into the peptide sequence. Similarly, the hydroxyls present on the glycosidic residues borne by the threonines must be suitably protected during the peptide synthesis.

Once the peptide synthesis has been carried out, the peptides are separated from the solid support and deprotected. They can be purified by reverse-phase High Performance Liquid Chromatography.

According to an advantageous arrangement of this embodiment, the glycosidic residues borne by the O-glycosylated threonines prepared in step i) are hexoses, preferably mannoses, the mannose residues advantageously being bonded to one another via α-(1,2) bonds.

According to an advantageous mode of this arrangement, the threonines functionalized with mannose residues are prepared as follows:

a$_2$) preparation of mannose derivatives of formulae (I) and (II):

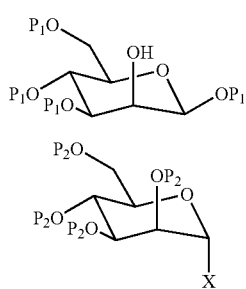

in which $P_1$ and $P_2$, which may be identical or different, represent groups which protect a hydroxyl function, and X represents an activated function, such as a bromine atom, b$_2$) reaction of the derivative of formula (I) with the derivative of formula (II), then activation of the compound obtained, leading to the production of an activated derivative comprising two mannose residues and corresponding to the formula (III):

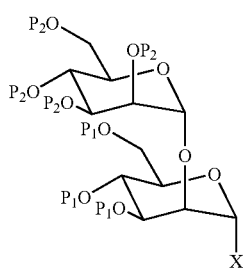

in which $P_1$, $P_2$ and X are as defined in relation to formulae (I) and (II), c$_2$) optionally, reaction of the compound of formula (III) with a mannose derivative of formula (I) as defined in a$_2$), then activation of the compound obtained, leading to the production of an activated derivative comprising three mannose residues and corresponding to the formula (IV):

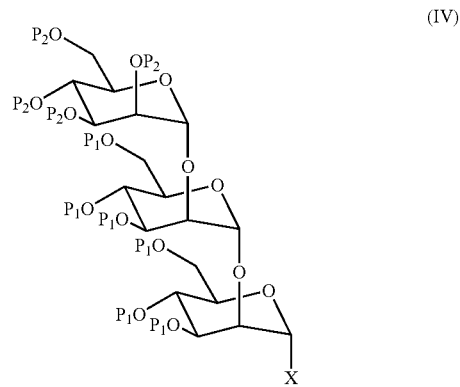

in which $P_1$, $P_2$ and X are as defined in relation to formulae (I) and (II), and d$_2$) condensation of the compound of formula (III) or of the compound of formula (IV) with a suitably protected threonine of formula (V):

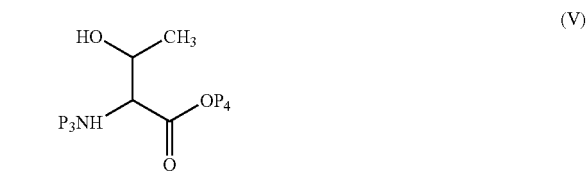

in which $P_3$ represents a group which protects a primary amine function and $P_4$ represents a group which protects a hydroxyl function, leading, respectively, to the production of a glycosylated threonine of formula (VI) or (VII):

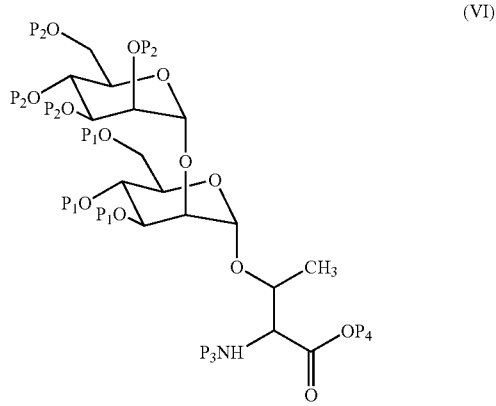

-continued

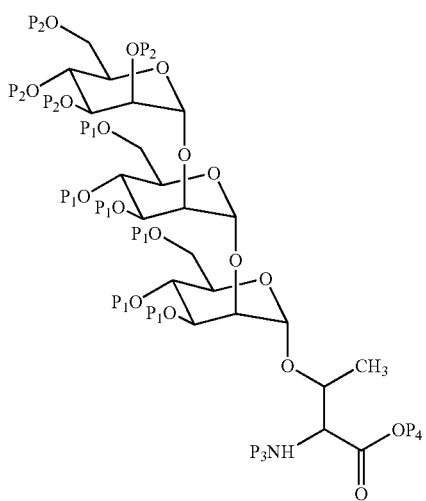

(VII)

in which $P_1$, $P_2$, $P_3$ and $P_4$ are as defined above.

The protective groups $P_1$, $P_2$, $P_3$ and $P_4$ may be chosen from those described in the work *Protective Groups in Organic Synthesis*, T. W. GREENE and P. G. M. WUTS, Second Edition, 1991, J. WILEY and Sons. By way of examples and in a nonlimiting manner, $P_1$ and $P_2$ may represent acetyl or benzoyl groups, $P_3$ may represent an Fmoc (9-fluorenylmethoxycarbonyl) group and $P_4$ may represent a pentafluorophenyl group.

A subject of the present invention is also a method for selecting and screening immunogenic glycopeptides using the peptide sequence of the proteins of a pathogenic microorganism, which may advantageously be carried out concomitantly with the method for synthesizing the glycopeptides in accordance with the invention, as defined above, which method is characterized in that it comprises at least the following steps:

$a_3$) searching for and selecting, in and from the peptide sequence of said proteins, at least one 14 to 25 amino acid sequence containing at least one neutral amino acid bonded to a disaccharide or a trisaccharide and at least 15% of proline, one of the prolines being located in position -1 to -4, relative to the position of said neutral amino acid, $b_3$) preparing the glycopeptide(s) selected in step $a_3$), in accordance with the method of synthesis defined above, and $c_3$) selecting the glycopeptides the antigenic activity of which is at least 10 times greater, preferably at least 30 times greater, than that of a control peptide with the same sequence.

According to an advantageous embodiment of said screening method, prior to step $a_3$), it comprises a step for preselecting at least one antigenic glycoprotein.

According to another advantageous embodiment of said screening method, in step $c_3$), the antigenic activity of said glycopeptide is evaluated by measuring the activity of the CD4+ T lymphocytes of animals immunized with said attenuated pathogenic microorganism or with an antigenic fraction of said pathogenic microorganism.

The activation of the T lymphocytes can be demonstrated using conventional immunology techniques, such as those described in *Current protocols in Immunology* (John E. Coligan, 2000, Wiley and son Inc, *Library of Congress, USA*). By way of example, mention may be made of lymphocyte proliferation assays, assays for the cytokines (protein or mRNA) synthesized by activated CD4+ T lymphocytes (immunoassay (ELISA) or polymerization chain reaction of the RT-PCR type) or, in the case of *M. tuberculosis*, delayed-type hypersensitivity assays.

The present invention also encompasses the glycopeptides which can be obtained using the selection and screening method as defined above.

A subject of the present invention is also the use of at least one glycopeptide in accordance with the invention or of a glycopeptide of sequence SEQ ID NO:11, for preparing an immunogenic or immunization composition or a diagnostic reagent.

The glycopeptides according to the invention which detect very specifically the cellular and/or humoral immunity induced by infection with a pathogenic microorganism, in particular *M. tuberculosis*, may advantageously be used for the diagnosis of tuberculosis by any technique which allows the detection of cellular immunity, this technique being known to those skilled in the art, per se. By way of example, mention may be made of T-lymphocyte proliferation assays and immunoenzymatic assays for cytokines specific for CD4+ T lymphocytes, in particular γ-IFN.

A subject of the present invention is also an immunogenic composition capable of inducing humoral and/or cellular immunity, characterized in that it comprises at least one glycopeptide as defined above, combined with at least one pharmaceutically acceptable vehicle.

Because of the cooperation between CD4+ T lymphocytes and CD8+ T lymphocytes or B lymphocytes in the setting up of a humoral or cellular immune response, the glycopeptides of the invention may advantageously be used as a transport protein (carrier) for any other immunization antigen in order to increase the effectiveness of the immunization against said antigen. This antigen/carrier combination advantageously makes it possible to facilitate the selection and the amplification of the B and T lymphocytes specific for the immunization antigen.

A subject of the present invention is also an immunization composition which is capable of inducing humoral and/or cellular immunity, characterized in that it comprises at least one glycopeptide as defined above, combined with at least one pharmaceutically acceptable vehicle and, optionally, with at least one adjuvant.

According to an advantageous embodiment of said immunogenic or immunization compositions, said glycopeptide is combined with a protein or a protein fragment comprising at least one B epitope, one T epitope of the CF4+ type or one T epitope of the CD8+ type.

For the purposes of the present invention, the terms "B epitope", "T epitope of the CD4+ type" and "T epitope of the CD8+ type", relative to the sequence of a protein, is intended to mean the fragment of this sequence which is capable of binding, respectively, to an antibody, to a T receptor of CD4+ lymphocytes and to a T receptor of CD8+ lymphocytes.

For the purposes of the present invention, the expression "combination of the glycopeptide with a protein" is intended to mean both mixing and coupling by any physical or chemical means, for example the expression of a fusion between the sequence of the glycopeptide and that of the protein or of the protein fragment.

The adjuvants used are conventionally used adjuvants; advantageously, they are chosen from the group consisting of aluminium hydroxide and squalene.

Said glycopeptide may optionally be combined with any other means, known per se to those skilled in the art, which makes it possible to increase the immunogenicity of a peptide. By way of example, mention may be made of coupling to a carrier peptide, which enables the production of a branched multimerized peptide, such as that described by Wilkinson et al., 1999, *Eur. J. Immunol.*, 29, 2788-2796.

A subject of the present invention is also antibodies, characterized in that they are directed against one or more of the glycopeptides according to the present invention.

According to an advantageous embodiment of said antibodies, they are selected from monoclonal antibodies and polyclonal antibodies.

A subject of the present invention is also a diagnostic reagent, characterized in that it is selected from the group consisting of the glycopeptides and the antibodies according to the invention.

A subject of the present invention is also a method for detecting an infection with a pathogenic microorganism, characterized in that it comprises bringing a biological sample from a patient likely to be infected with said pathogenic microorganism into contact with a diagnostic reagent as defined above (antibodies or glycopeptides, depending on the case) and detecting the formation of an antibody/microorganism present in the biological sample complex or a glycopeptide(s)/antibodies present in the sample complex.

A subject of the present invention is also a method for diagnosing an infection in a patient likely to be infected with a pathogenic microorganism, comprising the detection of CD4+ T lymphocytes recognizing at least one glycopeptide as defined above.

According to an advantageous implementation of said method, it comprises the steps of:
  administering said glycopeptide(s) to the patient, and
  detecting CD4+ T lymphocytes recognizing said glycopeptide(s).

According to another advantageous implementation of said method, it comprises the steps of:
  bringing a biological sample from said patient into contact with said glycopeptide(s), and
  detecting CD4+ T lymphocytes recognizing said glycopeptide(s).

The CD4+ T lymphocytes detection is carried out by any conventional immunology technique which measures the T cell response to an antigen, this technique being known to those skilled in the art. Advantageously, said detection is performed by using a lymphocyte proliferation assay, a cytokine assay (protein or mRNA), or a delayed-type hypersensitivity assay.

The proliferation assay may be based on Cell-Specific-Fluorescence-Extinction (CSFE) or tritiated thymidine incorporation. The cytokine assay may be carried out by ELISPOT, intracellular cytokine staining, ELISA or RT-PCR. The cytokine which are assayed include: IFN-γ, IL-2, IL-4, IL-5, IL-10, IL-12, IL-15.

The biological sample is a cell suspension containing T CD4+ positive cells. Advantageously, it is a suspension of peripheral blood mononuclear cells (PBMCs). Said biological sample, may be depleted of CD8+ positive cells or pre-enriched in T lymphocytes via a preliminary step of in vitro culturing of the cells in the presence of one or more glycopeptide(s) according to the invention.

According to another advantageous implementation of said method, it is a method for diagnosing tuberculosis, wherein said glycopeptide is derived from *M. tuberculosis*, preferably from the Apa or the Rv1796 protein, more preferably, said glycopeptide is selected from the group consisting of SEQ ID NO: 1, 2 or 3.

The *M. tuberculosis* derived glycopeptide(s) are advantageously administered to the patient, and the CD4+ T lymphocytes recognizing said glycopeptide(s) are detected by a delayed-type hypersensitivity assay.

Alternatively, a biological sample from said patient likely to be infected with *M. tuberculosis*, preferably a PBMCs suspension, is brought into contact with said glycopeptide(s), and the CD4+ T lymphocytes recognizing said glycopeptide(s) are detected by a proliferation assay or a cytokine assay.

Another subject of the present invention is a kit for diagnosing an infection in a patient likely to be infected with a pathogenic microorganism, comprising at least a glycopeptide as defined above.

According to an advantageous embodiment of said kit, it is a kit for diagnosing tuberculosis, comprising a glycopeptide derived from *M. tuberculosis*, as defined above.

Besides the arrangements above, the invention comprises even more arrangements, which will emerge from the following description which refers to examples of implementation of the present invention and also to the attached diagrams in which:

BRIEF DESCRIPTION OF THE DRAWINGS

FIG. 2 illustrates the mass spectrometry analysis of the mannose composition of the Apa molecules, as a function of the kinetics of digestion of the Apa protein with α-mannosidase. The number of mannose residues corresponding to each peak of the Apa protein is indicated and the overall antigenic activity of the product of the Apa digestion is indicated at the various times studied.

EXAMPLE 1

Figure 1:
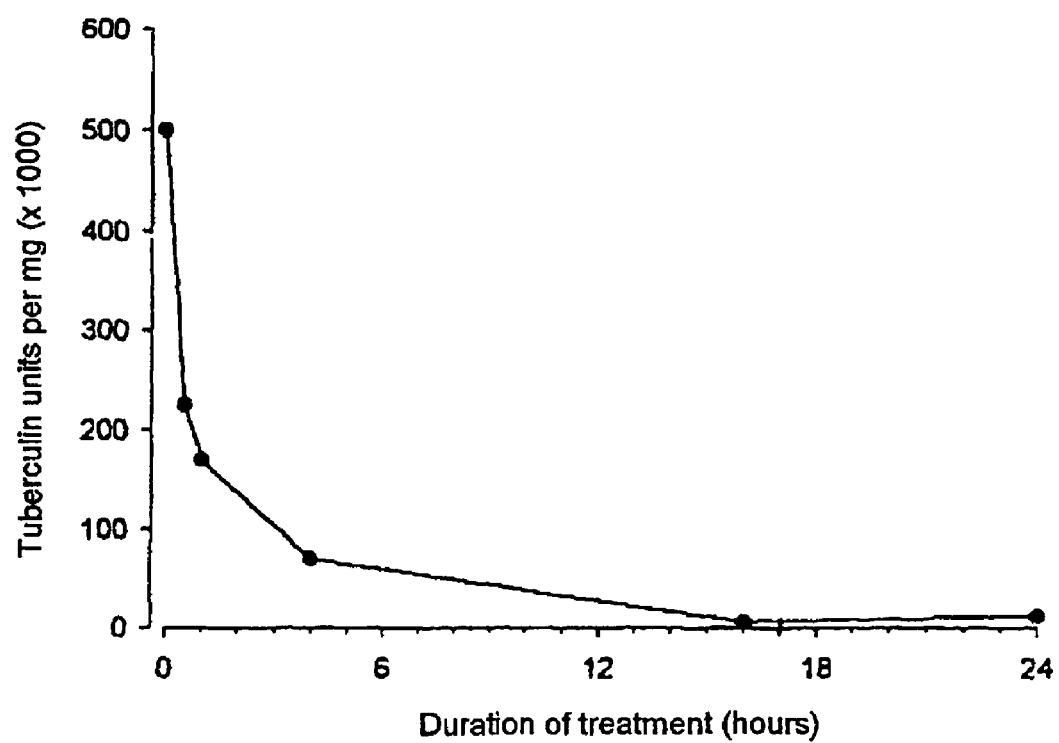
FIG. 1 illustrates the measurement, using a delayed-type hypersensitivity assay, of the antigenic activity of the native Apa purified from *M. tuberculosis*, as a function of the kinetics of digestion of the Apa protein by α-mannosidase. The results are expressed in tuberculin units per mg of protein as a function of time in hours.

Importance of the Number of Oligosaccharide Residues in the Antigenicity of the Apa Protein 1. Materials and Methods a) Limited Deglycosylation of Apa by Digestion with α-Mannosidase 450 μg of Apa protein purified from the culture supernatant of *M. tuberculosis*, according to the protocol described by Horn et al., mentioned above, are diluted in a 450 μl volume of buffer A (100 mM $CH_3COO^-Na^+$, 2 mM $ZnCl_2$).

At the initial timepoint, 75 μl of the Apa protein solution are removed, diluted in 25 μl of buffer A and frozen as a control. 125 μl of α-mannosidase at 1 mg/ml (3 IU/ml, Oxford Glycosciences) are then added to the 375 μl of the Apa solution and the 500 μl reaction volume is incubated at 37° C. After 30 min, 1 h, 4 h, 16 h and 24 h, 100 μl of the reaction are removed and frozen at −20° C.

b) Purification of the Digestion Products

The 100-μl samples are heated for 2 min at 90° C. and are then abruptly cooled, dried under vacuum and resuspended in 300 μl of trifluoroacetic acid at 0.1% in water (solution B).

The Apa digestion products are separated from the α-mannosidase on a reverse-phase chromatography column (Ressource RPC, Pharmacia), using a gradient of 0 to 90% acetonitrile in solution B, in 90 min. The Apa is eluted from the column at the time t=68 min, corresponding to 51.5%±0.5% of acetonitrile. The fractions corresponding to the Apa are collected, lyophilized, resuspended in a solution of butanol at 5% in water (solution C) and then dried under vacuum. The purified samples are then resuspended in 100 μl of solution C.

c) Biochemical Analysis of the Apa Digestion Products

The oligosaccharide composition of each sample is analysed by mass spectrometry under the conditions described in Horn et al., mentioned above.

The absorption at 210 nm is measured in order to evaluate the relative amount of protein present in each sample.

Next, the samples are dried and their concentration is adjusted to 1 mg/ml in a titration buffer (buffer D: PBS, 0.9% NaCl, 0.05% Tween 80).

d) Biological Titration of the Antigenic Activity of the Products of Limited Digestion of Apa with α-mannosidase, in a Delayed-Type Hypersensitivity Assay The antigenic activity is measured using a delayed-type hypersensitivity assay on guinea pigs immunized 3 months beforehand by an intradermal injection of 2 mg of live BCG at 2 injection points.

Each sample is diluted to a concentration of 2 μg/ml in buffer D and 100 μl of this dilution (0.2 μg) are injected intradermally into batches of 2 previously immunized guinea pigs.

The various batches of animals are as follows:
batch 1: negative control having received 100 μl of buffer D
batch 2: Apa t=0
batch 3: Apa t=30 min
batch 4: Apa t=1 h
batch 5: Apa t=4 h
batch 6: Apa t=16 h
batch 7: Apa t=24 h
batch 8: positive control (0.25 μg of standard purified proteins from *Mycobacterium tuberculosis* (PPD) corresponding to 10 tuberculin units (TU).

24 h after the injection, the mean of the erythema reaction diameter is measured for the various batches of animals and the tuberculin titre of the samples is determined with respect to the PPD standard.

2. Results

The results are illustrated by FIGS. 1 and 2.

The analysis of the antigenic activity of the Apa as a function of the kinetics of digestion with α-mannosidase (FIG. 1) shows that the antigenic activity of the Apa is gradually lost during the digestion with α-mannosidase: 66% in 1 h, 86% in 4 h and 97 to 99% for the longer digestions.

The analysis of the mannose composition of the products obtained at the various digestion times (FIG. 2) shows that:
the native Apa molecules have 6 to 8 mannose residues, and
the Apa molecules on which there remain 3 to 6 mannose residues lose 86% of their antigenic activity.

It has been shown that the oligomannose composition of Apa is as follows: a dimannose ($T_{10}$ and $T_{18}$), a mannose ($T_{27}$), a mannose, a dimannose or a trimannose ($T_{277}$), Dobos et al., mentioned above. In addition, α-mannosidase is an exomannosidase.

Consequently, the results indicate that:
the loss of 1 or 2 of the terminal mannoses of the 4 oligomannose chains of Apa causes a drastic loss of the antigenic activity, and
the antigenicity of Apa is linked to the presence of a dimannose or of a trimannose on one or more of the glycosylated threonine residues.

EXAMPLE 2

Demonstration of the Lip Glycopeptide of *M. tuberculosis*

1. Materials and Methods a) Purification of the Glycopeptide a1) Preparation of the Crude Material Bacteria of the *Mycobacterium tuberculosis* (H37Rv) strain are cultured for 20 days on a Sauton synthetic medium (culture medium, H. Cassagne, 1961, Ed. Institut Pasteur, volume 2, page 242). The molecules secreted into the medium are concentrated on an ultrafiltration membrane (PM10, AMICON) in such as way as to retain only the molecules of molecular mass greater than 10 000 Da, and then they are lyophilized. Approximately 10 g of lyophilisate are obtained for 60 litres of culture medium.

a2) Molecular Filtration (Step 1)

A preparative column is filled with Sup75 prepgrade matrix, Pharmacia. This 50×750 mm column is equilibrated with a phosphate buffer (50 mM $Na_2$/K $PO_4$, pH 7.1; 100 mM NaCl; 4% butanol) at a flow rate of 1 ml/min. The crude material above is taken up in the equilibration buffer at a final concentration of 10 g per 100 ml and clarified by centrifugation at 43 000 g for 4 h, then by filtration over a 0.22 μm filter. Injections of 13 ml are performed and the various fractions detected via their absorbence at 280 nm are concentrated on a PM10 membrane and then lyophilized.

The fraction eluted between 700 and 800 ml is very antigenic: delayed-type hypersensitivity is observed in guinea pigs immunized with live BCG; this fraction is, on the other hand, relatively inactive in guinea pigs immunized with heat-inactivated BCG.

a3) Ion Exchange (Step 2)

A 24×250 mm Pharmacia Source 15Q preparative column (15 μm) is equilibrated with a 20 mM tris/HCl, pH 8, 4% butanol buffer at a flow rate of 5 ml/min with a maximum pressure of 8 bar. A linear NaCl gradient of 0 to 150 mM in the same buffer is applied after injecting 500 mg of the fraction above dissolved in 10 ml of initial buffer. The fractions eluted are detected by absorption at 280 nm, concentrated on a PM10 membrane and then lyophilized.

The fraction eluted between 40 and 75 mM NaCl is very antigenic; delayed-type hypersensitivity is observed in guinea pigs immunized with live BCG; this fraction is, on the other hand, relatively inactive in guinea pigs immunized with heat-inactivated BCG.

a4) Reverse Phase on a C8 Column (Step 3)

A 4.6×100 mm Pharmacia RPC column (Reversed Phase Column) Resource 15RPC is equilibrated with a 20 mM $CH_3COO$—$NH_4^+$ buffer, pH 6.5, at a flow rate of 1 ml/min. A nonlinear acetonitrile gradient, of between 0 and 90%, is applied after injecting onto the column 10 mg of the fraction above, in 2 ml of buffer. The fractions eluted are detected at 280 nm and then concentrated under vacuum at 40° C. before being lyophilized.

The fraction eluted between the acetonitrile concentrations of 18 and 22% is very antigenic in terms of revealing delayed-type hypersensitivity in guinea pigs immunized with live BCG and relatively inactive in guinea pigs immunized with heat-inactivated BCG.

a5) Reverse Phase on a C18 Column (Step 4)

A C18 reverse-phase microbore column (Browlec lab. 1×250 mm) is equilibrated with a 20 mM $CH_3COO^-NH_4^+$ buffer, pH 6.5, at a flow rate of 1 ml/min. A nonlinear acetonitrile gradient of 0 to 90% is applied after injecting the fraction above onto the column.

A fraction detected only at 220 nm is eluted with a concentration of approximately 11% of acetonitrile. This fraction (3 mg) is very active in terms of revealing delayed-type hypersensitivity reactions in guinea pigs immunized with live bacteria and relatively inactive in guinea pigs immunized with heat-inactivated BCG.

b) Biochemical Analysis of the Purified Glycopeptide

The fraction obtained in the final purification step was sequenced using a modified Edman technique (Applied Biosystems 473A), according to the manufacturer's instructions.

The composition of each sample is analysed by mass spectrometry (MALDI-TOF spectrometer) under the conditions described by Horn et al., mentioned above.

c) Digestion of the Glycopeptide with α-mannosidase

9 μg of the glycopeptide purified above are dissolved in 65 μg of 100 mM $CH_3COO^-Na^+$ buffer, pH 5, and then 3 μl of a 1 mg/ml α-mannosidase solution (Oxford Glyco System), i.e. 90 mU of α-mannosidase, are added. The reaction is incubated for 24 h at 37° C. so as to obtain total digestion, and then the product obtained is dried under vacuum.

d) Digestion of the Peptide with Subtilisin 690 ng of the glycopeptide purified above are dissolved in 5 μl of 100 mM ammonium carbonate buffer, pH 8, and then 1 μl of a 100 μg/ml subtilisin solution, i.e. approximately 100 ng, is added. The reaction is incubated for 24 h at 37° C. and then the reaction product is dried under vacuum and taken up in the titration buffer (buffer D).

e) Biological Titration of the Antigenic Activity of the Glycopeptide using a Delayed-Type Hypersensitivity Assay 0.02 μg of the glycopeptide purified above, nondigested or digested with α-mannosidase or subtilisin, are injected in batches of previously immunized guinea pigs, according to the protocol described in Example 1. The results are expressed by the value of the erythema reaction diameter. The control consists of 0.25 μg of PPD, corresponding to 10 TU.

f) Measurement of the Antigenic Activity of the Glycopeptide using an in vitro Lymphocyte Proliferation Assay The conditions of the assay are those described in Horn et al., mentioned above.

2. Results a) Purification and Biochemical Analysis of the Lip Glycopeptide

The mass measurement performed on the purified glycopeptide indicates the presence of complex molecules probably glycosylated with mannoses, given the presence of measurements which differ by a value of 162 mass units. A mass of 6 951 Da, which corresponds to the mass of the peptide treated with α-mannosidase, is taken as the minimum mass of these molecules.

The N-terminal sequence of the purified glycopeptide indicates the presence of a major sequence TIPTT . . . and of a minor sequence IPTTE . . . .

These results are compatible with a mannosylated glycopeptide, termed Lip, the sequence (SEQ ID NO:3) of which is that of an N-terminal fragment of a peptide derived from the protein encoded by the Rv1796 gene of *M. tuberculosis*, which extends from positions 169 to 239 of said protein, with reference to the annotation of the sequence of the genome of *M. tuberculosis* strain H37Rv from the Sanger bank.

b) Measurement of the Antigenic Activity of the Lip Glycopeptide using a Delayed-Type Hypersensitivity Assay The glycopeptide is very active in terms of revealing delayed-type hypersensitivity reactions in guinea pigs immunized with live bacteria, on the other hand it is relatively inactive in guinea pigs immunized with heat-inactivated BCG.

The antigenic activity of the glycopeptide increases during the purification steps:

Step 1: The fraction obtained has an activity of 180 000 TU/mg in guinea pigs immunized with live BCG and of 10 000 TU/mg in guinea pigs immunized with heat-inactivated BCG.

Step 2: The fraction obtained has an activity of 900 000 TU/mg in guinea pigs immunized with live BCG and of 30 000 TU/mg in guinea pigs immunized with heat-inactivated BCG.

Step 3: The purified fraction has an activity of greater than 1 000 000 TU/mg in guinea pigs immunized with live BCG and of less than 30 000 TU/mg in guinea pigs immunized with heat-inactivated BCG.

Figure 3:
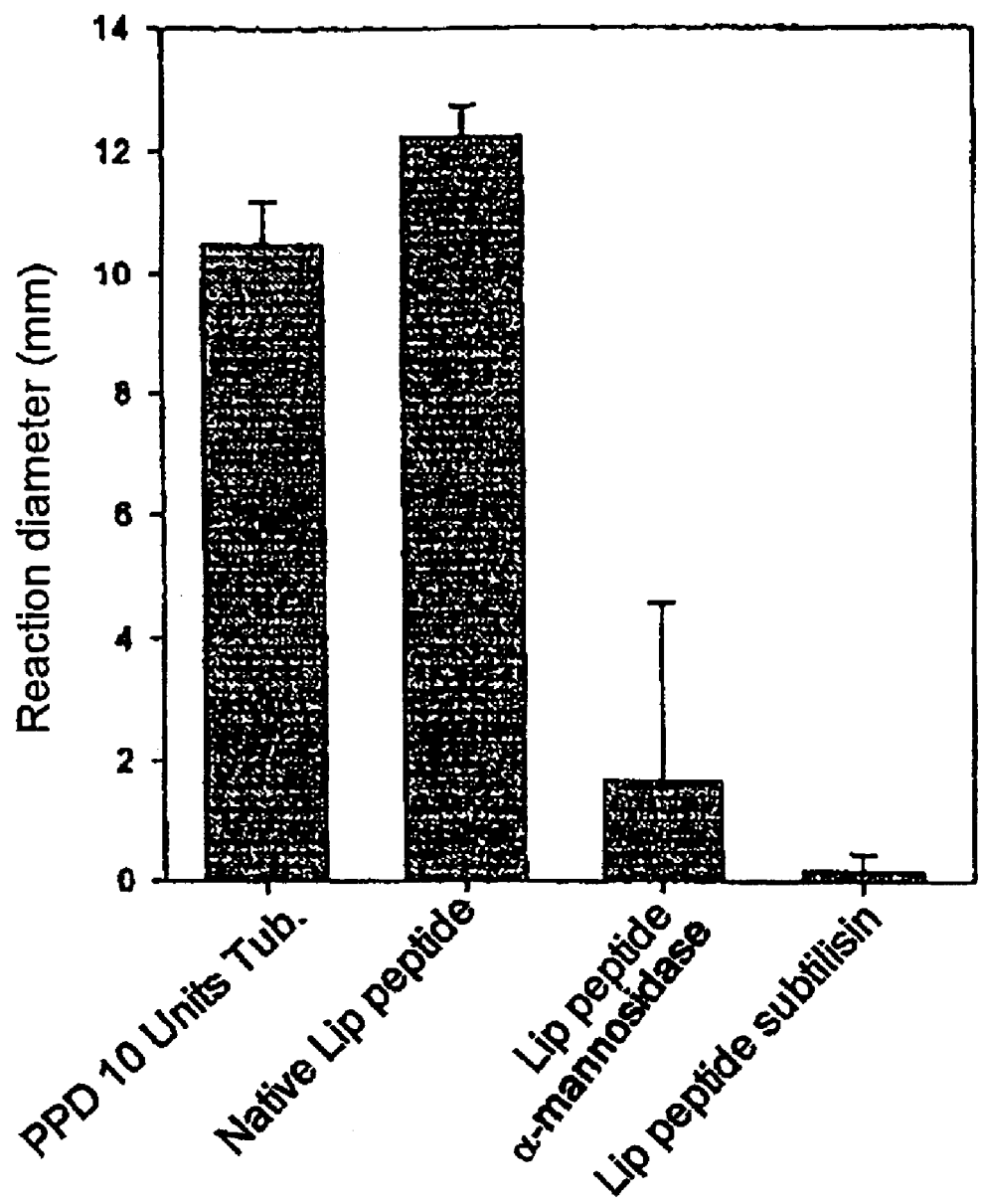
FIG. 3 illustrates the measurement, using a delayed-type hypersensitivity assay, of the antigenic activity of a glycopeptide, termed Lip, derived from the Rv 1796 protein (SEQ ID NO:3). The standard purified proteins from *M. tuberculosis* (PPD) are used as a positive control at the dose of 0.25 µg in 0.1 ml. The Lip peptide is used at the dose of 0.02 µg in 0.1 ml. The Lip peptides treated with α-mannosidase or subtilisin are negative at the same doses. The results are expressed by the erythema reaction diameter.
Figure 4:
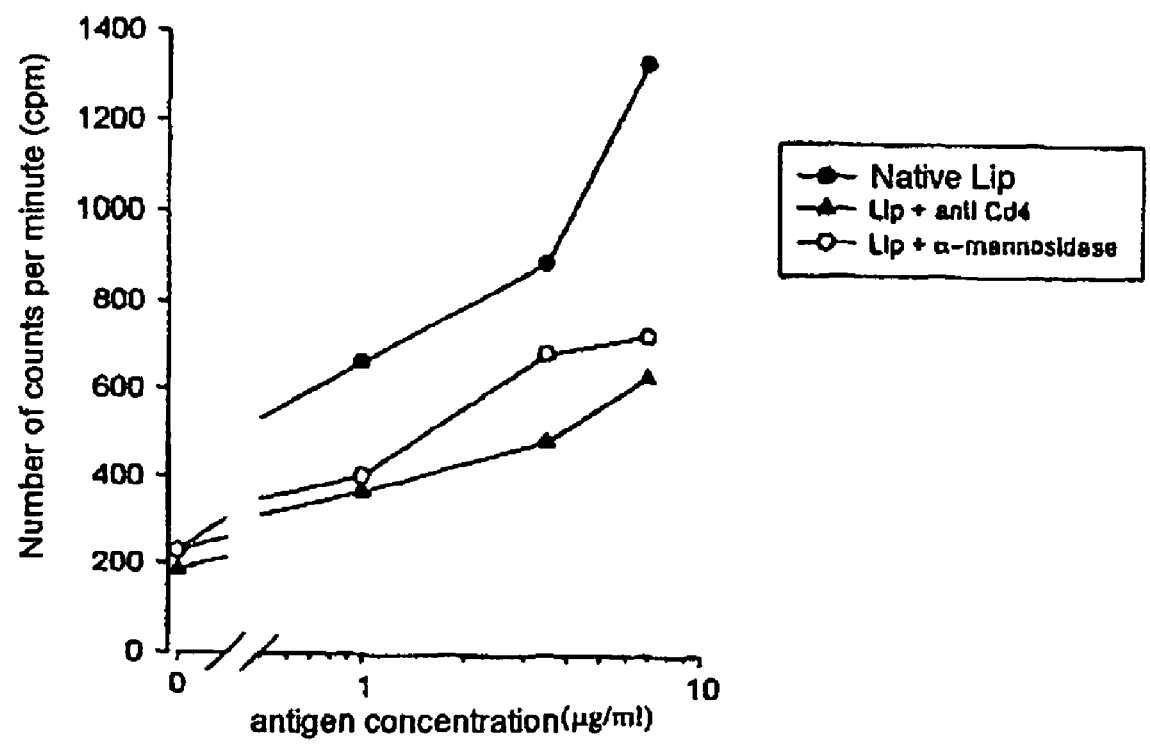
FIG. 4 illustrates the antigenic activity of the Lip peptide using an in vitro lymphocyte proliferation assay. The recognition of the glycosylated Lip peptide (native Lip) by the T lymphocytes is compared to that of the deglycosylated peptide (Lip+α-mannosidase) or of the Lip peptide combined with an anti-T-lymphocyte CD4+ receptor antibody (Lip+anti Cd4)

The results illustrated in FIG. 3 show that:

the action of α-mannosidase for 24 h at 37° C. causes a loss of more than 95% of the antigenic activity: the fraction dropped from an activity of 1 000 000 TU/mg to an activity of less than 30 000 TU/mg after deglycosylation, the action of subtilisin abolishes the antigenic activity, and at an equivalent amount of proteins, the Lip glycopeptide is at least 10 times more active than the standard purified proteins from *Mycobacterium tuberculosis* (PPD).

c) Measurement of the Antigenic Activity of the Lip Glycopeptide using an in vitro Lymphocyte Proliferation Assay The results illustrated in FIG. 4 show that the T-lymphocyte proliferation is dependent on the peptide concentration. This proliferation is marginal when the T lymphocytes are treated with an antibody directed against CD4 molecules or when the glycopeptide is treated with α-mannosidase.

EXAMPLE 3

Demonstration of the Role of the Oligosaccharide Residues of Apa in Defining T epitopes, by Immunization with Naked DNA Encoding the Apa Protein 1. Materials and Methods a) Construction of a Plasmid Containing the Sequence Encoding the Apa Protein The plasmid pS65T (Clontech) containing the sequence of the cytomegalovirus early promoter is cleaved with the NheI and BspEI restriction enzymes, repaired with the Klenow enzyme and then ligated so as to obtain the plasmid pAG800.

The plasmid pAG800 is cleaved with the ApaI enzyme and ligated with the oligonucleotide 12M48 (5' CAACGT-TGGGCC 3'; SEQ ID NO:4) hybridized to itself, so as to give the plasmid pAG802.

An 875 base pair fragment containing the coding sequence of Apa lacking the signal sequence is amplified, by polymerase chain reaction (PCR), from the plasmid pLA34-2 (Laqueyrerie, 1995, *Infect. Immun.*, 63, 4003-4010), using:

the oligonucleotides 22M42 (5' TCCCAAGCTTTTGG-TAGCCG 3'; SEQ ID NO:5) and 33M44 (5' CTAG-GATCCACCATGCCGGAGCCAGCGCCCCCG 3'; SEQ ID NO:6).

The oligonucleotide 33M44 was synthesized in such a way as to contain a consensus translation initiation site of the Kozak type (*Nucl. Acids Res.*, 1987, 15, 8125-8148). The fragment obtained by PCR is cleaved with BamHI and EcoRV and inserted into the plasmid pAG802 cleaved with BglII and SmaI, so as to give the plasmid pAG803. During these operations, the oligonucleotide sequence 5' CAACGTTGGGCC 3' (SEQ ID NO:4) is lost; this sequence, termed Psp1046 ISS, is considered to be an immunostimulant sequence which increases immune response in the same way as the sequence IL-12p40 ISS (Lipford G B et al., 1997, *Eur. J. Immunol.*, 27, 3420-3426).

A Psp1046 ISS sequence is inserted at the BamHI site of the plasmid pAG803 by cloning the oligonucleotide 25M45 (5' GATCCGGGGGGGAACGTTGGGGGGG 3'; SEQ ID NO:7) hybridized with the oligonucleotide 25M46 (5' GATC-CCCCCCCAACGTTCCCCCCCG 3'; SEQ ID NO:8), so as to obtain the plasmid pAG831.

An IL-12p40 ISS sequence is inserted at the BamHI site of the plasmid pAG803 by cloning the oligonucleotide 24M63 (5' AGCGCTATGACGTTCCAAGGGCCC 3'; SEQ ID NO:9) hybridized with the oligonucleotide 24M64 (5' GGGCCCTTGGAACGTCATAGCGCT 3'; SEQ ID NO:10), so as to obtain the plasmid pAG832.

After transforming *Escherichia coli* strain XL1 Blue, the plasmids above are amplified in LB culture medium (Sambrook et al., Molecular cloning: A laboratory Manual, Cold Spring Harbor Laboratory Press, Cold Spring Harbor, N.Y., 1989) containing 25 µg/ml of kanamycin. After a prior step for eliminating the endotoxin by treating the bacterial lysates with Triton X-114 (1%), the plasmid DNA is purified on MaxiPrep QIA filter columns (QIAGEN) according to the manufacturer's indications.

b) Immunization of Guinea Pigs with the Plasmids pAG831 and pAG832

Guinea pigs (Hartley) weighing 300 to 400 g are immunized with 50 µg of the DNA of the plasmids pAG831 or pAG832, prepared and purified as indicated above, by giving 2 intradermal injections into the flanks.

The control consists of a group of guinea pigs immunized with live BCG under the conditions described in Example 1 or in Example 2.

c) Measurement of the Antigenic Activity of the Apa Protein Produced by Eukaryotic Cells in Guinea Pigs Immunized with Naked DNA, using a Delayed-Type Hypersensitivity Assay One and two months after immunization, the delayed-type hypersensitivity reactions are measured with respect to the native Apa protein or to the recombinant Apa protein produced in a transformed strain of *Escherichia coli*, which proteins are purified according to the protocol described in Horn et al., mentioned above. The native Apa and the recombinant Apa are injected intradermally at the dose of 0.2 µg in 100 µl of titration buffer (buffer D). The antigenic activity is measured as described in Example 2.

2. Results

Figure 5:
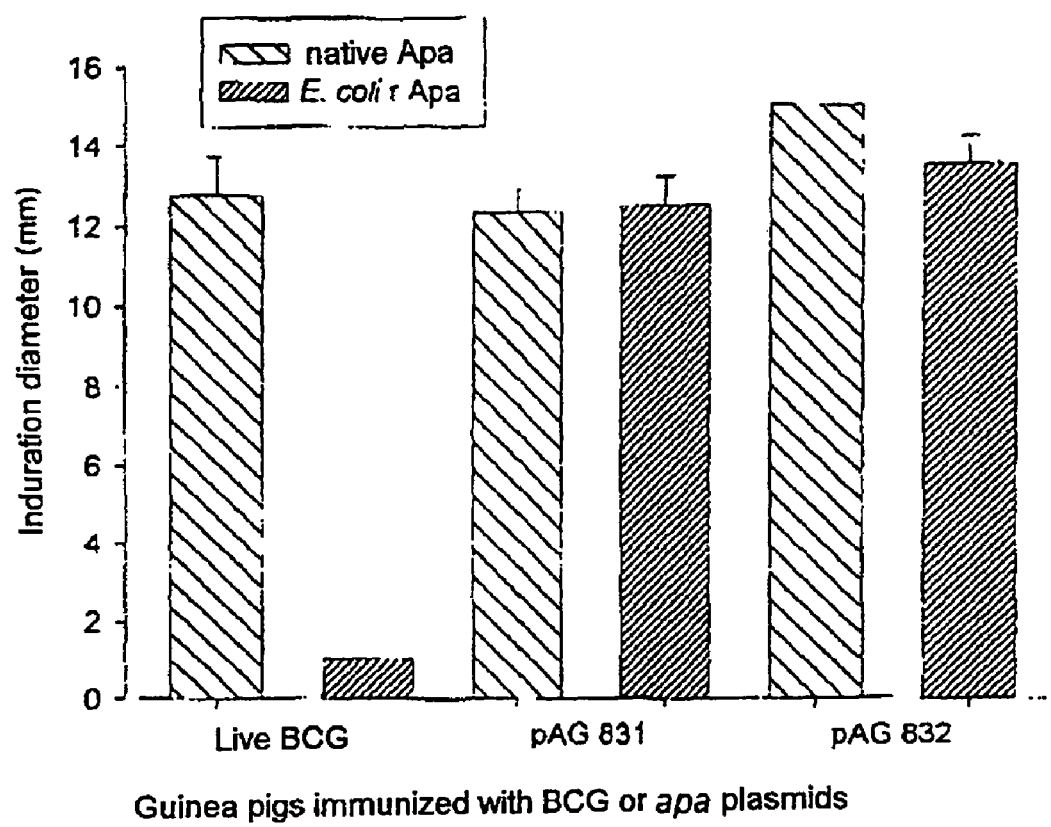
FIG. 5 illustrates the measurement, using a delayed-type hypersensitivity assay, of the antigenic activity of the native Apa purified from *M. tuberculosis* (native Apa) or of the deglycosylated recombinant Apa produced in *E. coli* (*E. coli* rApa), as a function of the immunization of guinea pigs. The latter were immunized beforehand with live BCG injected intradermally or with the plasmids pAG831 or pAG832, containing the coding sequence of Apa, placed under the control of the cytomegalovirus early promoter. The immunization of the guinea pigs with the plasmids produces a sensitization which can be revealed by a delayed-type hypersensitivity reaction. The two types of antigen are equivalent for engendering this reaction, whereas, after an immunization with BCG, only the glycosylated native Apa is antigenic.

The results illustrated by FIG. 5 are as follows:

The guinea pigs immunized with the plasmid pAG831 or pAG832 containing the coding sequence of Apa under the control of a eukaryotic promoter develop, in the vast majority of cases, an immune response directed against the native Apa protein (antibodies and a T-response of the CD4+ type which can be measured using a delayed-type hypersensitivity assay or an in vitro T-lymphocyte proliferation assay when they are brought together with the antigens). In the animals corresponding to the native Apa antigen, the CD4+ T lymphocyte responses against the antigen deglycosylated via the enzymatic pathway or against the non-glycosylated recombinant antigen originating from *E. coli* are of the same strength as the responses observed with the glycosylated native antigen.

On the other hand, the guinea pigs immunized with live BCG show a delayed-type hypersensitivity reaction only in response to the native Apa. These animals develop no reaction or develop a greatly decreased reaction in response to the non-glycosylated recombinant Apa produced in *E. coli* as indicated above.

These results provide the following teachings:

1) The results observed in the animals immunized with naked DNA encoding Apa indicate that the capacity of the Apa protein to be phagocytosed and presented by macrophages or dendritic cells is identical for the native or recombinant (non-glycosylated) Apa protein.

2) The combination of the results above with the results observed in the animals immunized with live BCG indicate that the absence of response to the deglycosylated Apa protein is not due to a decrease in its capacity to be presented by macrophages or dendritic cells, but to an absence of recognition by CD4+ T lymphocytes. Consequently, the oligomannose residues of the side chains of the Apa or Lip proteins in the native form, such as those produced by *M. tuberculosis* or by live BCG, play a role in the constitution of T epitopes recognized by CD4+ T lymphocytes.

EXAMPLE 4

Preparation of the Glycosylated Peptides SEQ ID NO:1, SEQ ID NO:2 and SEQ ID NO:3

1) Preparation of the Glycosylated Synthons 15, 16 and 19

Prior to the peptide synthesis, glycosylated synthons, i.e. threonines functionalized with two or three mannose residues, are prepared.

Figure 6:
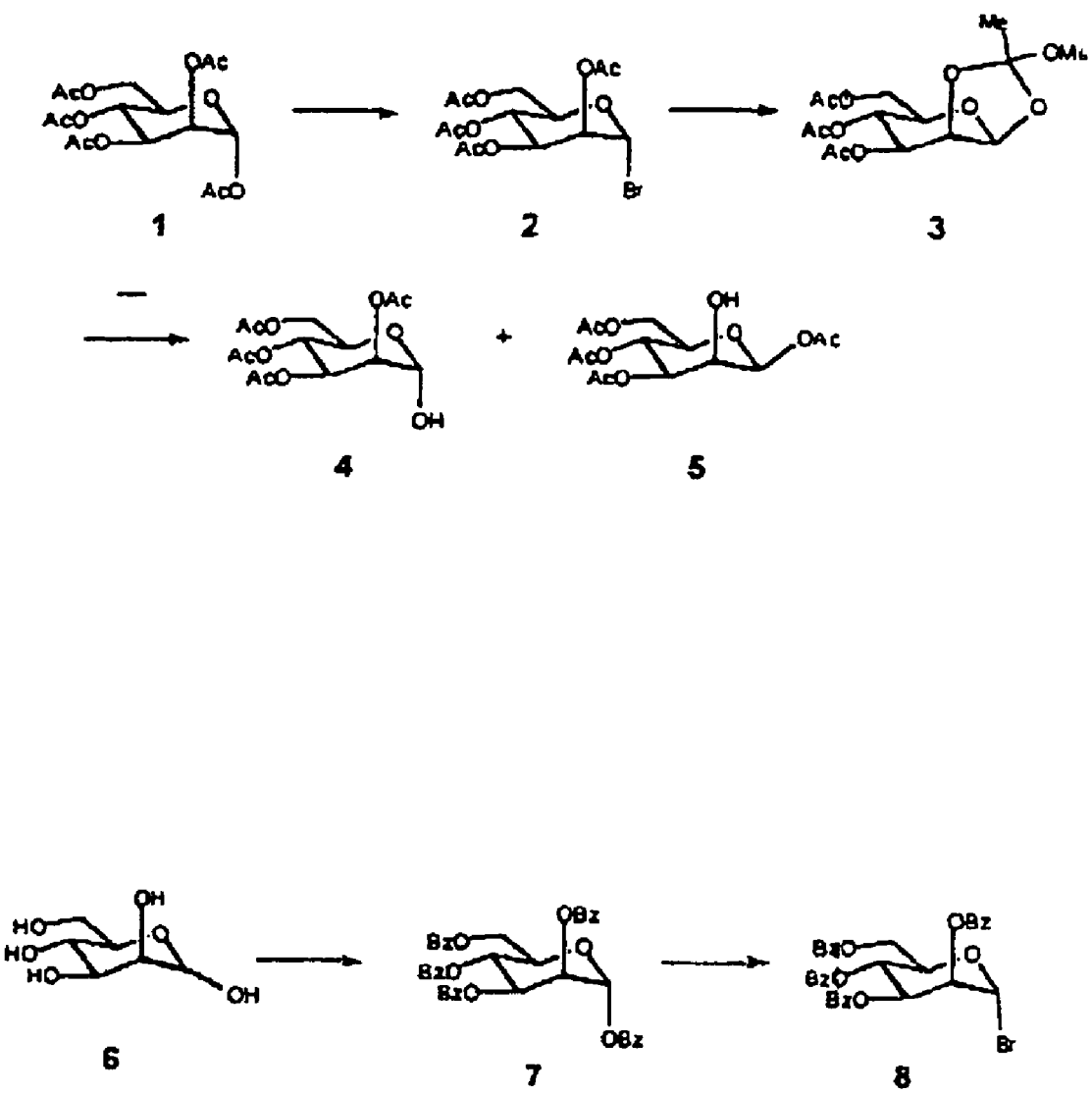
FIG. 6 represents the preparation of units comprising two or three mannose residues bonded via α-(1,2) bonds, and FIG. 7 (7a and 7b) represents the preparation of threonines functionalized with two or three mannose units.

Preparation of the Compounds 5 and 8 (FIG. 6)

The preparation of the compounds 5 and 8 is described by H. FRANZYK et al. in *J. Chem. Soc. Perkin Trans.* 1, 1995, 2883-2898 and by R. K. NESS et al., in *J. Am. Chem. Soc. Perkin*, 1950, 72, 2200-2205, respectively.

The commercial peracetylated mannose 1 (i.e. 1,2,3,4,5-penta-O-acetyl-α-D-mannopyranose) is brominated in the anomeric position by the action of hydrogen bromide in acetic acid, as described by A. LEVENE et al. in *J. Biol. Chem.*, 1931, 90, 89-98. The activated intermediate 2 is cyclized to the orthoester 3 in a 2,6-dimethylpyridine/methanol mixture. The regioselective opening of the orthoester by acid hydrolysis at 0° C. in a 10% aqueous trifluoroacetic acid/acetonitrile mixture produces 1,3,4,6-tetra-O-acetyl-β-D-mannopyranose (5). The regioisomer 4 is also isolated.

The commercial mannose 6 is perbenzoylated to 7 by the action of benzoyl chloride in pyridine. The latter is activated to 8 by the action of hydrogen bromide in acetic acid. In this protocol and in those which follow, activation methods other than by the action of hydrogen bromide may, however, be used, such as they are known to those skilled in the art.

Preparation of the Disaccharides 10 and 12 (FIG. 7a)

The preparation of the compounds 10 and 12 is described by A. JANSSON et al. in *J. Chem. Soc. Perkin Trans.* 1, 1992, 1699-1707 and by H. FRANZYK et al. (ibid), respectively. The compounds 2 and 5 are condensed in the presence of silver trifluoromethanesulphonate (or any other condensation reaction promoter) in dichloromethane so as to produce the peracetylated disaccharide 9, which is then activated to the brominated precursor 10 by the action of hydrogen bromide in acetic acid. According to an identical protocol, the compounds 5 and 8 are condensed to give the compound 11, itself activated to 12.

Preparation of the Trisaccharide 18 (FIG. 7a)

The activated disaccharide 12 is condensed onto the monosaccharide acceptor 5, in the presence of silver trifluoromethanesulphonate in dichloromethane, so as to produce the peracetylated trisaccharide 17, which is then activated to the brominated precursor 18 by the action of hydrogen bromide in acetic acid.

Preparation of the Synthons 15 and 16, Carrying Two Mannose Units, and of the Synthon 19, Carrying Three Mannose Units (FIG. 7b)

As described by I. SCHON et al. in *Synthesis*, 1986, 303-305, the acid function of the commercial threonine 13, the primary amine function of which is protected by an Fmoc group, is blocked in the form of an ester by the action of pentafluorophenol (pfp) in the presence of dicyclohexylcarbodiimide (DCCI) so as to produce the acceptor precursor 14.

The preparation of the synthons 15 and 16 is described by A. JANSSON et al. (ibid) and by H. FRANZYK et al. (ibid), respectively. The condensation of the compound 14 with the activated disaccharides 10 and 12, carried out in the presence of silver trifluoromethanesulphonate in dichloromethane, produces the synthons 15 and 16, respectively. According to the same protocol, the condensation of the compound 14 with the activated trisaccharide 18 produces the synthon 19.

2) Preparation of the Glycosylated Peptides SEQ ID NO:1, SEQ ID NO:2 and SEQ ID NO:3

The peptides are synthesized in solid phase using Fmoc chemistry. The peptide synthesis is performed on an automatic synthesizer, using the amino acids required for producing the desired sequences, while incorporating the glycosylated synthons, which are in the form of activated esters of pentafluorophenol (synthons 15, 16 and 19).

Depending on the synthons used, either peptides comprising threonines functionalized with two mannose residues (incorporation of the synthons 15 and/or 16 during the peptide synthesis) or peptides comprising threonines functionalized with three mannose residues (incorporation of the synthon 19 during the peptide synthesis) or peptides comprising both threonines functionalized with two mannose residues and threonines functionalized with three mannose residues (incorporation of the synthons 19 and 15 and/or 16 during the peptide synthesis) are obtained.

At the end of synthesis, after cleavage of the peptides from the solid support using trifluoroacetic acid and deprotection of the various amino acids and of the hydroxyl functions of the mannoses, the peptides are purified by reverse-phase High Performance Liquid Chromatography (HPLC). Their structure is controlled using techniques known to those skilled in the art, such as mass spectrometry and amino acid analysis.

The amide functions (in the C-terminal position of the peptides SEQ ID NO:1 and SEQ ID NO:3, and acetate functions (in the N-terminal position of the peptides SEQ ID NO:2 and SEQ ID NO:3) are then introduced by chemical synthesis, using organic chemistry techniques known to those skilled in the art.

EXAMPLE 5

Demonstration of the Role of the Oligosaccharide Residuals of Apa in Defining T Epitopes, by Immunization with an Apa Peptide produced in *E. coli*

1) Materials and Methods

A peptide corresponding to positions 250 to 280 of Apa was produced in *E. coli*, in the form of a fusion with a fragment of *Bordetella pertussis* cyclase, according to the conventional techniques of cloning, expression and purification of recombinant proteins in *E. coli* which are well known to those skilled in the art (cf. for example, the protocols described in *Current Protocols in Molecular Biology* (Frederick M. AUSUBEL, 2000, Wiley and Son Inc, Library of Congress, USA).

Three groups of 5 Hartley guinea pigs weighing 300 to 400 g were immunized, with 2 intradermal injections one month apart, with 20 µg of this purified Apa peptide, in 0.1 ml of an adjuvant solution.

Three groups of 4 guinea pigs immunized four months beforehand with live BCG, under the conditions described in example 1, are used as controls.

One and two months after immunization, delayed hypersensitivity reactions were measured with respect to the native Apa protein, to the recombinant Apa protein produced in *E. coli* and to the deglycosylated Apa protein prepared as described in example 1, under the conditions defined in example 3.

2) Results

The delayed hypersensitivity reactions of the guinea pigs immunized either with the Apa fusion peptide or with the live BCG were measured with respect to the native Apa protein, to the recombinant Apa protein produced in E. coli and to the deglycosylated Apa protein. The results expressed by the diameter of the erythema reaction (mm) are given in table I below:

TABLE I

Antigenic activity of the Apa fusion peptide expressed in E. coli

| Antigen | Live BCG | Fusion peptide |
|---|---|---|
| Native Apa | 17-15-11-13 | 5-12-13-5-5 |
| E. Coli recombinant Apa | 0 0 0 0 | 13-14-15-5-15 |
| Deglycosylated Apa | 0 0 0 0 | NT* |

*NT: not tested

As indicated in table I above, the delayed hypersensitivity reactions observed in the guinea pigs immunized with live BCG are considerable after injection of native Apa molecules. The reactions are very weak or absent after injection of the chemically deglycosylated molecules or of the molecules produced in E. coli. On the other hand, for the guinea pigs immunized with the recombinant molecules corresponding to the fusion between the fragment of Bordetella pertussis cyclase and the internal fragment of the Apa molecule, the sensitizations are identical with respect to the native or deglycosylated molecules.

These results show that the glycosylated T epitopes of the Apa molecule are selectively recognized by the guinea pigs immunized with the live bacteria. They also show that the lack of, or reduced, recognition of the deglycosylated molecules by the guinea pigs is not associated with a reduced intrinsic antigenicity of these molecules.

EXAMPLE 6

Diagnosis of Tuberculosis by a CD4+ T Lymphocyte Proliferation Assay using an Apa Glycopeptide 1) Material and Methods
  a) Material
  All the monoclonal antibodies are from BECKMAN COULTER: CD45/CD4/CD8/CD3 (# 6607013); CD8-PC5 (# 6607011); CD4-ECD (# 6604727); CD25-RD1 (# 6604422); CD45RO-PE (# IM1307); CD45RA-ECD (# IM2711); TCR PAN-PC5 αβ (# IM2661); TCR PAN-PC5 γδ (#IM2662); CD3-PE (IM 1282); Flow Count (# 7547053); Immunoprep (# 7546999).
  b) Methods
  PBMC Preparation
  Peripheral blood mononuclear cells were isolated by Ficoll gradient centrifugation, according to standard protocols. Mononuclear cells numeration, and T lymphocytes, T CD4+ and T CD8+ percentages determination, were determined by flow cytometry, using a panel of antibody, directed to the following cell surface antigens: CD45, CD4, CD8 and CD3.
  Cell Stimulation
  The isolated mononuclear cells were cultured for six days in RPMI (GIBCO) supplemented with 20% AB serum (VAL-BIOTECH), at 37° C., in a 9% $CO_2$ incubator, in the presence or in the absence of one of the following antigen preparations:
    PPD: standard purified proteins from M. tuberculosis (10 mg/ml)
    native Apa (10 µg/ml)
    deglycosylated Apa (10 µg/ml)
    synthetic glycosylated peptide SEQ ID NO: 1 (2 µg/ml)

Stimulation was made in triplicate.

Detection of the Apa-Specific Cd4+ T Lymophocytes Response in a Roliferation Assay Based on CSFE Dilution Cells previously labelled with CSFE, according to the manufacturer instructions (BIOPROBES) and stimulated or not, with the different antigen preparations, were incubated for 30 min at room temperature, with the following combinations of antibodies: CD3-PE/CD4-ECD/CD8-PC5; CD45-RA-ECD/CD45-RO-PE/TCRαβb-PC5; CD25-PE/TCR6-PC5 and fixed with PBS-2% paraformaldehyde. CD4+ T lymphocytes proliferation was evaluated by measuring the loss of the CFSE fluorescence by flow cytometry.

Detection of the Apa-Specific Cd4+ T Lymphocytes Response in a Proliferation Assay Based on Tritiated Thymidine Incorporation.

Cells stimulated or not, with the different antigen preparations, were incubated for 18 h in the presence of 1 µCi $^3$H-thymidine, in RPMI+10% AB serum. The cells were then lysed and $^3$H-thymidine incorporation in the cells was measured by beta-scintillation counting.

Detection of the Apa-Specific Cd4+ T Lymphocytes Response in a Cytokine-ELISA Assay Two days after the stimulation with the different antigen preparations, the culture supernatant was harvested and the cytokines (IFN-γ, IL-2, IL-4, IL-5, IL-10, IL-12 and IL-15) were assayed by ELISA using commercial kits.

Population/Statistical Analysis

Twelve BCG-vaccinated healthy individuals (controls) and 18 tuberculosis patients (M. tuberculosis infected individuals presenting the clinical signs of tuberculosis disease) were tested. The results were analysed with the Mann-Whitney U test, a more sensitive nonparametric alternative to the t-test for independent samples. A p value<0.05 corresponds to a significant difference between the controls and the patients groups.

2) Results

Figure 8:
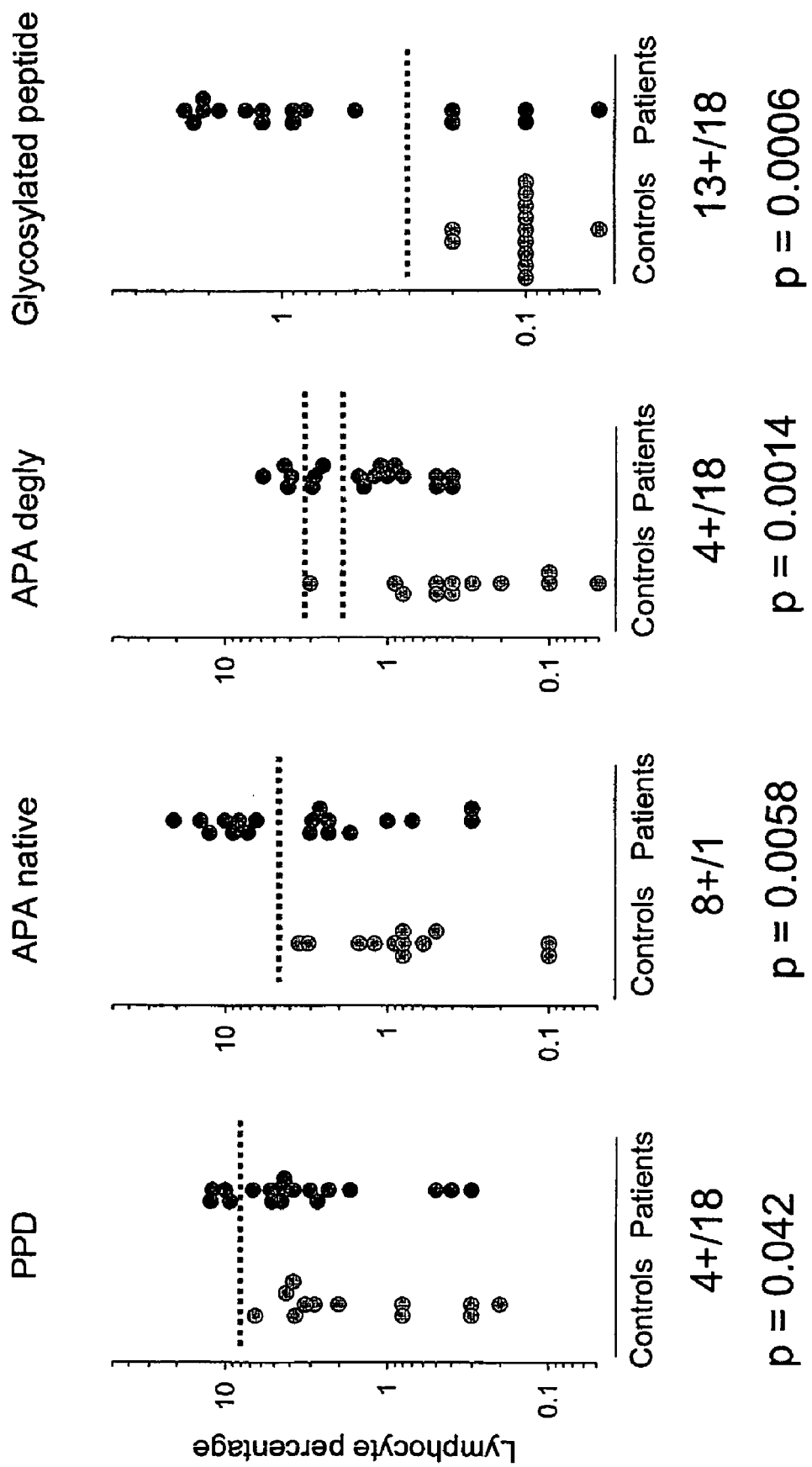
FIG. 8 illustrates CD4+ lymphocytes proliferation of vaccinated subjects (controls) or tuberculosis patients (patients), in the presence of the Apa derived glycopeptide SEQ ID NO: 1, by comparison with native or deglycosylated Apa, and standard purified proteins from *M. tuberulosis* (PPD), measured by cellular specific fluorescence extinction (CSFE). The statistical analysis is performed with the Mann-Whitney test (p value<0.05 corresponds to a significative difference between the patients and the controls). The proportion of patients which are considered positive in the assay is indicated.

The results of the CD4+ T lymphocytes proliferation assay based on CSFE dilution are presented in FIG. 8.

Stimulation with PPD does not allow to differentiate the response from the vaccinated and the tuberculosis patients.

The native Apa antigen stimulates more frequently the response from the patients as compared with the vaccinate controls (8 positive/18 patients); this difference between the groups is lost with the deglycosylated antigen.

By contrast, the glycosylated Apa peptide stimulates the CD4+ T lymphocytes from the majority of patients (13/18) and does not stimulate the CD4+ lymphocytes from the controls.

Therefore, the glycopeptide is useful for diagnosing active tuberculosis or primo-infections with M. tuberculosis, in a T CD4+ proliferation assay or in a cytokine production assay.

As emerges from the above, the invention is in no way limited to its methods of implementation, preparation and application which have just been described more explicitly; on the contrary, it encompasses all the variants thereof which may occur to a person skilled in the art, without departing from the context or scope of the present invention.

The invention claimed is:

1. A method for diagnosing tuberculosis in a patient, the method comprising the step of:

detecting a *M. tuberculosis* Apa protein-specific CD4+ T lymphocyte response in vivo or in vitro in said patient, wherein said CD4+ T lymphocyte response is directed to a glycopeptide consisting of SEQ ID NO:1 which extends from position 1 to 39 of the *M. tuberculosis* Apa protein sequence, and in which at least one threonine at position 10, 18 and 27 of SEQ ID NO:1 is bonded to a dimannose or trimannose via a glycosidic bond, and wherein said detected CD4+ T lymphocyte response is indicative of tuberculosis in said patient and differentiates tuberculosis from an immunization with BCG (Bacillus Calmette-Guérin).

2. The method according to claim 1, comprising the steps of:

administering said glycopeptide to the patient, and detecting said CD4+ T lymphocyte response directed to said glycopeptide.

3. The method according to claim 1, comprising the steps of:

bringing a biological sample from said patient into contact with said glycopeptide, and detecting said CD4+ T lymphocyte response directed to said glycopeptide.

4. The method according to claim 1, wherein said detection is carried out by a lymphocyte proliferation assay.

5. The method according to claim 1, wherein said detection is carried out by a cytokine assay.

6. The method according to claim 2, wherein said detection is carried out by a delayed-type hypersensitivity assay.

7. The method according to claim 3, wherein said biological sample consists of peripheral blood mononuclear cells.

8. The method according to claim 1, wherein said dimannose or trimannose comprises an α-(1,2) glycosidic bond.

* * * * *